(12) United States Patent
Whang et al.

(10) Patent No.: US 8,779,023 B2
(45) Date of Patent: Jul. 15, 2014

(54) IN SITU FORMATION OF NANOPARTICLES IN RESINS

(75) Inventors: Kyumin Whang, Helotes, TX (US); H. Ralph Rawls, San Antonio, TX (US); Barry Norling, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 69 days.

(21) Appl. No.: 13/162,454

(22) Filed: Jun. 16, 2011

(65) Prior Publication Data

US 2011/0306699 A1 Dec. 15, 2011

Related U.S. Application Data

(63) Continuation-in-part of application No. PCT/US2009/068320, filed on Dec. 16, 2009.

(60) Provisional application No. 61/138,001, filed on Dec. 16, 2008.

(51) Int. Cl.
*A01N 59/16* (2006.01)
*A61L 27/16* (2006.01)
*A61L 27/54* (2006.01)

(52) U.S. Cl.
CPC ........... *A01N 59/16* (2013.01); *A61L 2300/624* (2013.01); *A61L 2300/104* (2013.01); *A61L 2400/12* (2013.01); *A61L 27/16* (2013.01); *A61L 2300/404* (2013.01); *A61L 27/54* (2013.01)
USPC ............................ 523/113; 523/115; 523/120

(58) Field of Classification Search
USPC ......................................... 523/113, 115, 120
See application file for complete search history.

(56) References Cited

U.S. PATENT DOCUMENTS

| 3,672,942 | A | * | 6/1972 | Neumann | 427/295 |
| 6,267,590 | B1 | * | 7/2001 | Barry et al. | 433/8 |
| 6,716,895 | B1 | * | 4/2004 | Terry | 523/122 |
| 6,759,431 | B2 | * | 7/2004 | Hunter et al. | 514/449 |
| 2003/0134933 | A1 | | 7/2003 | Jin et al. | |
| 2005/0013842 | A1 | * | 1/2005 | Qiu et al. | 424/423 |
| 2005/0203237 | A1 | * | 9/2005 | Cornelius Maria Dekkers et al. | 524/450 |
| 2008/0181931 | A1 | * | 7/2008 | Qiu et al. | 424/429 |
| 2009/0074705 | A1 | * | 3/2009 | Graham et al. | 424/78.17 |

FOREIGN PATENT DOCUMENTS

WO WO-2008037991 A1 4/2008

OTHER PUBLICATIONS

Silver-Nanoparticle-Embedded Antimicrobial Paints, Kumar et al., Published online Jan. 20, 2008, Nature Materials.*
Silver-nanoparticle Embedded Antimicrobial Paints Based on Vegatable Oil, Kumar et al., Nature, Jan. 20, 2008.*
Furno et al., Journal of Antimicrobial Chemotherapy, Vo. 54, Issue 6, pp. 1019-1024 (2004).

* cited by examiner

*Primary Examiner* — James J Seidleck
*Assistant Examiner* — Peter A Salamon
(74) *Attorney, Agent, or Firm* — Winstead PC

(57) ABSTRACT

Methods of forming antimicrobial polymeric materials comprising metallic nanoparticles are disclosed. Such methods generally comprise: combining a metal-containing material with a resin in situ; and curing the resin in the presence of a metal-containing material. Antimicrobial polymeric materials formed by said methods are also disclosed.

15 Claims, 23 Drawing Sheets

IN SITU FORMATION OF NANOPARTICLES IN RESINS

CROSS-REFERENCES TO RELATED APPLICATIONS

The present application is a continuation-in-part of PCT/US2009/068320 filed Dec. 16, 2009, which claims priority from U.S. Provisional Patent Application No. 61/138,001 filed Dec. 16, 2008, which is hereby incorporated by reference as if fully set forth herein.

TECHNICAL FIELD

The present invention relates to antimicrobial agents. The present invention also relates to processes for making and using antimicrobial agents.

HISTORY OF RELATED ART

Surface microbial infestation in medical devices and other materials can result in serious infection, device failure, and even death of a patient. For instance, surface-centered infections have been implicated in food spoilage, spread of food-borne diseases, and bio-fouling of materials. To prevent such adverse effects, materials with antimicrobial characteristics have been used in many applications. For instance, antimicrobial materials have been used in medical devices, such as catheters, prosthetics, implants, and ophthalmic devices. However, such materials have limited efficacies. Furthermore, such materials can be expensive and time consuming to manufacture. Hence, there is a continuing significant interest in the further development of more effective antimicrobial materials that are manufactured in more efficient and cost effective manners.

SUMMARY OF THE INVENTION

In some embodiments, methods are disclosed for forming antimicrobial polymeric materials that comprise metallic nanoparticles. Such methods generally comprise: (1) combining a metal-containing material with a resin in situ; and (2) curing the resin in the presence of the metal-containing material to form the polymeric material. In some embodiments, the metal-containing material is a silver-containing material, such as silver benzoate. In some embodiments, the resin is an acrylic resin, such as poly (methyl methacrylate) (PMMA). In some embodiments, the curing comprises chemical curing, such as by treating the resin with benzoyl peroxide (BPO) and dimethylparatoluidine (DMPT). Other embodiments of the present disclosure provide antimicrobial polymeric materials produced by the foregoing methods.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

A more complete understanding of the methods and compositions of the present invention may be obtained by reference to the following Detailed Description when taken in conjunction with the accompanying Drawings, wherein.

DETAILED DESCRIPTION OF EXEMPLARY EMBODIMENTS

Figure 1:
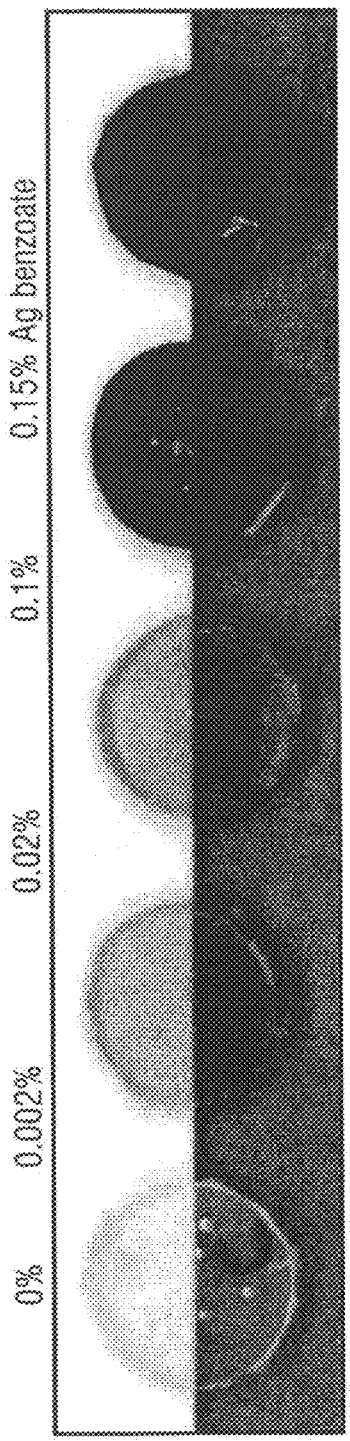
FIG. 1 illustrates photographs of light-cured (LC) samples with different Ag benzoate (AgB) concentrations.

In the following description, certain details are set forth such as specific quantities, sizes, etc. so as to provide a thorough understanding of the present embodiments disclosed herein. However, it will be understood by those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

The following definitions and explanations are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, 3rd Edition. Definitions and/or interpretations should not be incorporated from other patent applications, patents, or publications, related or not, unless specifically stated in this specification or if the incorporation is necessary for maintaining validity.

Other than in the operating examples, or where otherwise indicated, all numbers expressing quantities of components used herein are to be understood as modified in all instances by the term "about".

The present disclosure pertains to methods of forming antimicrobial polymeric materials that comprise in situ generated metallic nanoparticles. In some embodiments, such polymeric materials are formed by combining a metal-containing material with a resin in situ and then curing the resin in the presence of the metal-containing material. Other aspects of the present disclosure pertain to antimicrobial polymeric materials that comprise the above-mentioned in situ generated metallic nanoparticles.

As used herein, the term, "antimicrobial" means that the article exhibits one or more of the following properties: the inhibition of the adhesion of bacteria or other microbes to the article; the inhibition of the growth of bacteria or other microbes on the article; and/or the killing of bacteria or other microbes on the surface of the article or in an area surrounding the article. For purposes of this invention, adhesion of bacteria or other microbes to the article, the growth of bacteria or other microbes on the article and the presence of bacterial or other microbes on the surface of the article are collectively referred to as "microbial colonization." In various embodiments, the articles of the present disclosure exhibit at least about 0.25 log reduction, at least about 0.5 log reduction, or at least about a 1.0 log reduction (90% inhibition) of viable bacteria or other microbes. Such bacteria or other microbes include but are not limited to *Pseudomonas aeruginosa, Acanthamoeba* species, *Staphyloccus aureus, Escherichia coli, Staphyloccus epidermidis, Serratia marcesens, Acinetobacter baumannii* and/or the like.

As used herein, the term "patient" means and refers to a human or animal. Suitable examples include, but are not limited to a human or an animal (e.g., a dog, a cat, a horse, a bird, a reptile, an amphibian, a fish, a turtle, a guinea pig, a hamster, a rodent, a cow, a pig, a goat, a primate, a monkey, a chicken, a turkey, a buffalo, an ostrich, a sheep, a llama).

As used herein, the term "chemically feasible" refers to a connectivity of atoms such that the chemical valency of each atom is satisfied. For example, an oxygen atom with two bonds and a carbon atom with four bonds are chemically feasible.

As used herein, the term "nanoparticle(s)" means and refers to small particles ranging from small visible particles to particles on the nano-scale. As used herein, the term "metallic nanoparticle(s)" means and refers to nanoparticles that contain one or more metals, such as silver.

As used herein, the term "polymeric" means and refers to a composition(s) that comprises one or more monomers, oligomers, polymers, copolymers, or blends thereof. Suitable examples of polymers include, but are not limited to, polyvinyl alcohol, poly ethylene glycol, ethyl cellulose, polyolefins, polyesters, nonpeptide polyamines, polyamides, polycarbonates, polyalkenes, polyvinyl ethers, polyglycolides, cellulose ethers, polyvinyl halides, polyhydroxyalkanoates, polyanhydrides, polystyrenes, polyacrylates, polymethacrylates, polyurethanes, polypropylene, polybutylene terephthalate, polyethylene terephthalate, nylon 6, nylon 6,6, nylon 4,6, nylon 12, phenolic resins, urea resins, epoxy resins, silicone polymers, polycarbonates, polyethylene vinylacetate, polyethylene ethyl acrylate, polylactic acid, polysaccharides, polytetrafluoroethylene, polyvinylidenes, polyphosphazines, chlorinated polyethylenes, polysulfones and copolymers and blends thereof. Applicants also note that the terms "polymeric", "polymer" and "resin" may be used interchangeably in the present disclosure.

As used herein, the term "water soluble" or use of the term "miscible in water" means and refers to a level of solubility such that when a composition is placed in water, greater than about 2.0 percent by weight of the composition dissolves. For example, methyl methacrylate (MMA) is considered substantially non water soluble, yet has a water solubility of about 1.6 g in 100 g of water.

Currently, polymeric materials, such as polymethyl methacrylate (PMMA), are used in many industries for numerous purposes. For instance, polymeric resin materials are used in dentistry, orthopedics and craniofacial surgery. However one major problem with the utilization of polymeric resin materials is the occurrence of infections (e.g., caries in dentistry). For example, but not by way of limitation, approximately 10% of soldiers returning from various battlefields develop infections after receiving craniofacial implants. Likewise, failure of orthopedic implants is often due to the periprosthetic infections of the PMMA bone cement. Current therapies to treat the more severe cases of infections involve the use of local and systemic antibiotics. However, antibiotic therapy poses the problem of generating resistant strains of bacteria.

In the military, this is of special concern because many troops returning from various battlefields are infected with *Acinetobacter baumannii*, a multi-antibiotic resistant bacteria.

Accordingly, antimicrobial agents have been added to many polymeric materials in order to prevent infections during their various uses. For instance, silver salts have been used in human healthcare and medicine as an antiseptic for post surgical infections. Silver salts have also been used as an anti-microbial agent for various purposes in dental devices, wound therapy, medical devices, and/or the like. Specifically, silver nitrate has been used to prevent ophthalmic neonatorum in newborns.

More recently, silver compounds have been added to medical devices in various forms, including soluble and insoluble salts, complexes with binding polymers, zeolites, metallic silver, and oxidized silver. In addition, several techniques for the incorporation of silver into polymeric matrices have been disclosed, including: chemical workups, such as reduction or synthesis of complex silver compounds; mixing preformed silver particles with polymers; sputtering; and plasma deposition. The incorporation of oligodynamic metal salts, such as silver salts, as colloidal metal salt particles into medical devices has also been disclosed.

However, current techniques for incorporating antimicrobial agents into polymeric materials have limitations. For instance, dispersing the silver nanoparticles is detrimental to mechanical properties and/or curing the monomers. This is not surprising because silver and silver ions interact with free-radicals and can interfere with curing and/or negatively affect mechanical properties of resins when trying to incorporate particles and/or nanoparticles of silver into the resin.

Furthermore, various attempts to incorporate silver into monomer mixtures have met with problems in the prior art, such as, but not limited to dispersing the silver nanoparticles, which is detrimental to mechanical properties and/or curing the monomers. Silver and silver ions interact with free-radicals and can interfere with curing and/or negatively affect mechanical properties of resins when trying to incorporate particles and/or nanoparticles of silver into the resin.

Currently, there are no acrylate-based resins with silver nanoparticles (AgNP) on the market, possibly due to the above-mentioned limitations in prior art attempts to satisfactorily incorporate the AgNP into the acrylate-based resin. Further issues include, but are not limited to the other techniques, additional time, cost, multistep synthesis and complexity in the overall process of fabricating metal-particle-containing materials.

Accordingly, Applicants have developed novel methods of forming antimicrobial polymeric materials and novel resulting products and compositions of matter. In some embodiments, the present disclosure provides methods of forming an antimicrobial polymeric material that comprises a metallic nanoparticle. Such methods generally comprise: (1) combining a metal-containing material with a resin in situ; and (2) curing the resin in the presence of the metal-containing material.

By generating the metallic nanoparticle in situ, Applicants are able to cure monomer compositions more effectively than the prior art. In addition, prior art compositions that are light-cured have not cured as well with increased silver concentration, while those embodiments of the present invention that are chemically-cured are able to cure with a higher concentration of silver in the resin.

As explained below, numerous metal containing materials and resins may be used in various embodiments of the present disclosure. Likewise, various curing methods may be used to form the polymeric materials of the present disclosure.

Metal Containing Materials

A person of ordinary skill in the art will recognize that various metal containing materials may be used with the methods and compositions of the present disclosure. Non-limiting examples include antimicrobial metal-containing materials (which may or may not also be an atomically disordered crystalline material or a nanocrystalline material). More specific examples include silver-containing materials (e.g., silver, silver alloys, silver oxides, silver carbides, silver nitrides, silver borides, silver borate, silver sulfides, silver myristates, silver stearates, silver oleates, silver gluconates, silver adipates, silver silicates, silver phosphides, silver halides, silver hydrides, silver nitrates, silver carbonates, silver sulfadiazines, silver acetates, silver lactates, silver citrates, alkali silver thiosulphates (e.g., sodium silver thiosulphate, potassium silver thiosulphate)).

In some embodiments, metal containing materials may be silver salts that are soluble in organic solvents and acrylic monomers. In more specific embodiments, metal containing materials may be silver oleates, silver gluconates, silver adipates, silver sulfadiazines, silver acetates, silver benzoate and the like. In further embodiments, the metal containing material is silver benzoate By way of background, silver has been known for its broad-spectrum, antimicrobial activity as well as its wound healing properties. Furthermore, and as described in more detail below, Applicants' preliminary results have shown steady release of silver ions over 28 days, formation of inhibitory zones of bacterial growth, and over 95% growth inhibition of *S. aureus* with resins comprising as little as 0.5% silver.

However, Applicants note that the metal containing materials of the present disclosure are not limited to silver-containing materials. For instance, in other embodiments of the present disclosure, a metal containing material may be a gold-containing material. Such gold containing materials can include, without limitation, gold, gold alloys, gold oxides, gold carbides, gold nitrides, gold borides, gold sulfides, gold myristates, gold stearates, gold oleates, gold glutonates, gold glutonates, gold adipates, gold silicates, gold phosphides, gold halides, gold hydrides, gold nitrates, gold carbonates, gold sulfadiazines, gold acetates, gold lactates, gold citrates, alkali gold thiosulphates (e.g., sodium gold thiosulphate, potassium gold thiosulphate).

Similarly, in other embodiments, a metal containing material may be a platinum-containing material. Non-limiting examples include platinum, platinum alloys, platinum oxides, platinum carbides, platinum nitrides, platinum borides, platinum sulfides, platinum myristates, platinum stearates, platinum oleates, platinum glutonates, platinum adipates, platinum silicates, platinum phosphides, platinum halides, platinum hydrides, platinum nitrates, platinum carbonates, platinum sulfadiazines, platinum acetates, platinum lactates, platinum citrates, and alkali platinum thiosulphates (e.g., sodium platinum thiosulphate, potassium platinum thiosulphate).

Similarly, in other embodiments, a metal containing material may be a palladium-containing material. Non-limiting examples include palladium, palladium alloys, palladium oxides, palladium carbides, palladium nitrides, palladium borides, palladium sulfides, palladium myristates, palladium stearates, palladium oleates, palladium glutonates, palladium glutonates, palladium adipates, palladium silicates, palladium phosphides, palladium halides, palladium hydrides, palladium nitrates, palladium carbonates, palladium sulfadiazines, palladium acetates, palladium lactates, palladium citrates, and alkali palladium thiosulphates (e.g., sodium palladium thiosulphate, potassium palladium thiosulphate).

Metal containing materials of the present disclosure can also be iridium-containing materials, such as iridium, iridium alloys, iridium oxides, iridium carbides, iridium nitrides, iridium borides, iridium sulfides, iridium myristates, iridium stearates, iridium oleates, iridium glutonates, iridium glutonates, iridium adipates, iridium silicates, iridium phosphides, iridium halides, iridium hydrides, iridium nitrates, iridium carbonates, iridium sulfides, iridium sulfadiazines, iridium acetates, iridium lactates, iridium citrates, and alkali iridium thiosulphates (e.g., sodium iridium thiosulphate, antimicrobial potassium iridium thiosulphate).

Other suitable metal containing materials that can be used with various embodiments of the present disclosure include zinc-containing materials, such zinc, zinc alloys, zinc oxides, zinc carbides, zinc nitrides, zinc borides, zinc sulfides, zinc myristates, zinc stearates, zinc oleates, zinc glutonates, zinc glutonates, zinc adipates, zinc silicates, zinc phosphides, zinc halides, zinc hydrides, zinc nitrates, zinc carbonates, zinc sulfides, zinc sulfadiazines, zinc acetates, zinc lactates, zinc citrates, and alkali zinc thiosulphates (e.g., sodium zinc thiosulphate, potassium zinc thiosulphate).

Other suitable metal containing materials for the present disclosure include copper-containing materials, such as copper, copper alloys, copper oxides, copper carbides, copper nitrides, copper borides, copper sulfides, copper myristates, copper stearates, copper oleates, copper glutonates, copper glutonates, copper adipates, copper silicates, copper phosphides, copper halides, copper hydrides, copper nitrates, copper carbonates, copper sulfides, copper sulfadiazines, copper acetates, copper lactates, copper citrates, and alkali copper thiosulphates (e.g., sodium copper thiosulphate, potassium copper thiosulphate)).

Suitable metal containing materials for the present disclosure can also include tin-containing materials, such as tin, tin alloys, tin oxides, tin carbides, tin nitrides, tin borides, tin sulfides, tin myristates, tin stearates, tin oleates, tin glutonates, tin glutonates, tin adipates, tin silicates, tin phosphides, tin halides, tin hydrides, tin nitrates, tin carbonates, tin sulfides, tin sulfadiazines, tin acetates, tin lactates, tin citrates, and alkali tin thiosulphates (e.g., sodium tin thiosulphate, potassium tin thiosulphate)).

Suitable metal containing materials for the present disclosure can also include antimony-containing materials, such as antimony, antimony alloys, antimony oxides, antimony carbides, antimony nitrides, antimony borides, antimony sulfides, antimony myristates, antimony stearates, antimony oleates, antimony glutonates, antimony glutonates, antimony adipates, antimony silicates, antimony phosphides, antimony halides, antimony hydrides, antimony nitrates, antimony carbonates, antimony sulfides, antimony sulfadiazines, antimony acetates, antimony lactates, antimony citrates, and alkali antimony thiosulphates (e.g., sodium antimony thiosulphate, potassium antimony thiosulphate)), Suitable metal containing materials for the present disclosure can also include bismuth containing materials, such as bismuth, bismuth alloys, bismuth oxides, bismuth carbides, bismuth nitrides, bismuth borides, bismuth sulfides, bismuth myristates, bismuth stearates, bismuth oleates, bismuth glutonates, bismuth glutonates, bismuth adipates, bismuth silicates, bismuth phosphides, bismuth halides, bismuth hydrides, bismuth nitrates, bismuth carbonates, bismuth sulfides, bismuth sulfadiazines, bismuth acetates, bismuth lactates, bismuth citrates, and alkali bismuth thiosulphates (e.g., sodium bismuth thiosulphate, potassium bismuth thiosulphate)).

While the preceding paragraph lists certain metal-containing materials that may be anti-microbial, similar metal-containing materials (oxides, carbides, nitrides, borides, sulfides, myristates, stearates, oleates, glutonates, adipates, silicates, phosphides, halides, hydrides, nitrates, hydroxides, carbonates, sulfides, sulfadiazines, acetates, lactates, citrates and/or alkali metal thiosulphates of silver, gold, palladium, platinum, tin, iridium, antimony, bismuth, copper, zinc, selenium) can be anti-biofilm materials, antibacterial materials, anti-inflammatory materials, antifungal materials, antiviral materials, anti-autoimmune materials, anti-cancer materials, pro-apoptosis materials, anti-proliferatives, and/or MMP modulating materials.

Examples of nanocrystalline metal-containing materials (which may or may not also be an antimicrobial material or an atomically disordered crystalline material) include: nanocrystalline silver-containing materials (e.g., nanocrystalline silver, nanocrystalline silver alloys, nanocrystalline silver oxides, nanocrystalline silver carbides, nanocrystalline silver nitrides, nanocrystalline silver borides, nanocrystalline silver sulfides, nanocrystalline silver halides, nanocrystalline silver myristates, nanocrystalline silver stearates, nanocrystalline silver oleates, nanocrystalline silver glutonates, nanocrystalline silver glutonates, nanocrystalline silver adipates, nanocrystalline silver silicates, nanocrystalline silver phosphides, nanocrystalline silver hydrides, nanocrystalline silver nitrates, nanocrystalline silver carbonates, nanocrystalline silver sulfides, nanocrystalline silver sulfadiazines, nanocrystalline silver acetates, nanocrystalline silver lactates, nanocrystalline silver citrates, nanocrystalline alkali silver thiosulphates (e.g., nanocrystalline sodium silver thiosulphate, nanocrystalline potassium silver thiosulphate)); nanocrystalline gold-containing materials (e.g., nanocrystalline gold, nanocrystalline gold alloys, nanocrystalline gold oxides, nanocrystalline gold carbides, nanocrystalline gold nitrides, nanocrystalline gold borides, nanocrystalline gold sulfides, nanocrystalline gold halides, nanocrystalline gold hydrides, nanocrystalline gold nitrates, nanocrystalline gold myristates, nanocrystalline gold stearates, nanocrystalline gold oleates, nanocrystalline gold glutonates, nanocrystalline gold glutonates, nanocrystalline gold adipates, nanocrystalline gold silicates, nanocrystalline gold phosphides, nanocrystalline gold carbonates, nanocrystalline gold sulfides, nanocrystalline gold sulfadiazines, nanocrystalline gold acetates, nanocrystalline gold lactates, nanocrystalline gold citrates, nanocrystalline alkali gold thiosulphates (e.g., nanocrystalline sodium gold thiosulphate, nanocrystalline potassium gold thiosulphate)); nanocrystalline platinum-containing materials (e.g., nanocrystalline platinum, nanocrystalline platinum alloys, nanocrystalline platinum oxides, nanocrystalline platinum carbides, nanocrystalline platinum nitrides, nanocrystalline platinum borides, nanocrystalline platinum sulfides, nanocrystalline platinum myristates, nanocrystalline platinum stearates, nanocrystalline platinum oleates, nanocrystalline platinum glutonates, nanocrystalline platinum glutonates, nanocrystalline platinum adipates, nanocrystalline platinum silicates, nanocrystalline platinum phosphides, nanocrystalline platinum halides, nanocrystalline platinum hydrides, nanocrystalline platinum nitrates, nanocrystalline platinum carbonates, nanocrystalline platinum sulfides, nanocrystalline platinum sulfadiazines, nanocrystalline platinum acetates, nanocrystalline platinum lactates, nanocrystalline platinum citrates, nanocrystalline alkali platinum thiosulphates (e.g., nanocrystalline sodium platinum thiosulphate, nanocrystalline potassium platinum thiosulphate)); nanocrystalline palladium-containing materials (e.g., nanocrystalline palladium, nanocrystalline palladium alloys, nanocrystalline palladium oxides, nanocrystalline palladium carbides, nanocrystalline palladium nitrides, nanocrystalline palladium borides, nanocrystalline palladium sulfides, nanocrystalline palladium myristates, nanocrystalline palladium stearates, nanocrystalline palladium oleates, nanocrystalline palladium glutonates, nanocrystalline palladium glutonates, nanocrystalline palladium adipates, nanocrystalline palladium silicates, nanocrystalline palladium phosphides, nanocrystalline palladium halides, nanocrystalline palladium hydrides, nanocrystalline palladium nitrates, nanocrystalline palladium carbonates, nanocrystalline palladium sulfides, nanocrystalline palladium sulfadiazines, nanocrystalline palladium acetates, nanocrystalline palladium lactates, nanocrystalline palladium citrates, nanocrystalline alkali palladium thiosulphates (e.g., nanocrystalline sodium palladium thiosulphate, nanocrystalline potassium palladium thiosulphate)); nanocrystalline iridium-containing materials (e.g., nanocrystalline iridium, nanocrystalline iridium alloys, nanocrystalline iridium oxides, nanocrystalline iridium carbides, nanocrystalline iridium nitrides, nanocrystalline iridium borides, nanocrystalline iridium sulfides, nanocrystalline iridium myristates, nanocrystalline iridium stearates, nanocrystalline iridium oleates, nanocrystalline iridium glutonates, nanocrystalline iridium glutonates, nanocrystalline iridium adipates, nanocrystalline iridium silicates, nanocrystalline iridium phosphides, nanocrystalline iridium halides, nanocrystalline iridium hydrides, nanocrystalline iridium nitrates, nanocrystalline iridium carbonates, nanocrystalline iridium sulfides, nanocrystalline iridium sulfadiazines, nanocrystalline iridium acetates, nanocrystalline iridium lactates, nanocrystalline iridium citrates, nanocrystalline alkali iridium thiosulphates (e.g., nanocrystalline sodium iridium thiosulphate, nanocrystalline potassium iridium thiosulphate)); nanocrystalline zinc-containing materials (e.g., nanocrystalline zinc, nanocrystalline zinc alloys, nanocrystalline zinc oxides, nanocrystalline zinc carbides, nanocrystalline zinc nitrides, nanocrystalline zinc borides, nanocrystalline zinc sulfides, nanocrystalline zinc myristates, nanocrystalline zinc stearates, nanocrystalline zinc oleates, nanocrystalline zinc glutonates, nanocrystalline zinc glutonates, nanocrystalline zinc adipates, nanocrystalline zinc silicates, nanocrystalline zinc phosphides, nanocrystalline zinc halides, nanocrystalline zinc hydrides, nanocrystalline zinc nitrates, nanocrystalline zinc carbonates, nanocrystalline zinc sulfides, nanocrystalline zinc sulfadiazines, nanocrystalline zinc acetates, nanocrystalline zinc lactates, nanocrystalline zinc citrates, nanocrystalline alkali zinc thiosulphates (e.g., nanocrystalline sodium zinc thiosulphate, nanocrystalline potassium zinc thiosulphate)); nanocrystalline copper-containing materials (e.g., nanocrystalline copper, nanocrystalline copper alloys, nanocrystalline copper oxides, nanocrystalline copper carbides, nanocrystalline copper nitrides, nanocrystalline copper borides, nanocrystalline copper sulfides, nanocrystalline copper myristates, nanocrystalline copper stearates, nanocrystalline copper oleates, nanocrystalline copper glutonates, nanocrystalline copper glutonates, nanocrystalline copper adipates, nano crystalline copper silicates, nano crystalline copper phosphides, nanocrystalline copper halides, nanocrystalline copper hydrides, nanocrystalline copper nitrates, nanocrystalline copper carbonates, nanocrystalline copper sulfadiazines, nanocrystalline copper acetates, nanocrystalline copper lactates, nanocrystalline copper citrates, nanocrystalline alkali copper thiosulphates (e.g., nanocrystalline sodium copper thiosulphate, nanocrystalline potassium copper thiosulphate)); nanocrystalline tin-containing materials (e.g., nanocrystalline tin, nanocrystalline tin alloys, nanocrystalline tin oxides, nanocrystalline tin carbides, nanocrystalline tin nitrides, nanocrystalline tin borides, nanocrystalline tin sulfides, nanocrystalline tin myristates, nanocrystalline tin stearates, nanocrystalline tin oleates, nanocrystalline tin glutonates, nanocrystalline tin glutonates, nanocrystalline tin adipates, nanocrystalline tin silicates, nanocrystalline tin phosphides, nanocrystalline tin halides, nanocrystalline tin hydrides, nanocrystalline tin nitrates, nanocrystalline tin carbonates, nanocrystalline tin sulfides, nanocrystalline tin sulfadiazines, nanocrystalline tin acetates, nanocrystalline tin lactates, nanocrystalline tin citrates, nanocrystalline alkali tin thiosulphates (e.g., nanocrystalline sodium tin thiosulphate, nanocrystalline potassium tin thiosulphate)); nanocrystalline antimony-containing materials (e.g., nanocrystalline antimony, nanocrystalline antimony alloys, nanocrystalline antimony oxides, nanocrystalline antimony carbides, nanocrystalline antimony nitrides, nanocrystalline antimony borides, nanocrystalline antimony sulfides, nanocrystalline antimony myristates, nanocrystalline antimony stearates, nanocrystalline antimony oleates, nanocrystalline antimony glutonates, nanocrystalline antimony glutonates, nanocrystalline antimony adipates, nanocrystalline antimony silicates, nanocrystalline antimony phosphides, nanocrystalline antimony halides, nanocrystalline antimony hydrides, nanocrystalline antimony nitrates, nanocrystalline antimony carbonates, nanocrystalline antimony sulfides, nanocrystalline antimony sulfadiazines, nanocrystalline antimony acetates, nanocrystalline antimony lactates, nanocrystalline antimony citrates, nanocrystalline alkali antimony thiosulphates (e.g., nanocrystalline sodium antimony thiosulphate, nanocrystalline potassium antimony thiosulphate)); and nanocrystalline bismuth containing materials (e.g., nanocrystalline bismuth, nanocrystalline bismuth alloys, nanocrystalline bismuth oxides, nanocrystalline bismuth carbides, nanocrystalline bismuth nitrides, nanocrystalline bismuth borides, nanocrystalline bismuth sulfides, nanocrystalline bismuth myristates, nanocrystalline bismuth stearates, nanocrystalline bismuth oleates, nanocrystalline bismuth glutonates, nanocrystalline bismuth glutonates, nanocrystalline bismuth adipates, nanocrystalline bismuth silicates, nanocrystalline bismuth phosphides, nanocrystalline bismuth halides, nanocrystalline bismuth hydrides, nanocrystalline bismuth nitrates, nanocrystalline bismuth carbonates, nanocrystalline bismuth sulfides, nanocrystalline anti bismuth sulfadiazines, nanocrystalline bismuth acetates, nanocrystalline bismuth lactates, nanocrystalline bismuth citrates, nanocrystalline alkali bismuth thiosulphates (e.g., nanocrystalline sodium bismuth thiosulphate, nanocrystalline potassium bismuth thiosulphate)).

Resins

A person of ordinary skill in the art will also recognize that various resins may be used with the methods and compositions of the present disclosure. Non-limiting examples include acrylic resins. Acrylic resins include, but are not limited to, any resin containing an acrylate group (=CR—COOR'), where R and R' can be hydrogen, methyl, ethyl, butyl, benzoyl, or any alkyl or aryl group that is chemically feasible.

Other examples of resins that may be used with various embodiments of the present disclosure includes poly (methyl methacrylate) (PMMA) resins (an oil-based acrylic resin), other oil-based resins, water soluble resins, and/or the like.

More specific examples of resins that can be used with various embodiments of the present disclosure include, without limitation: Bis-GMA (bisphenol glycidyl methacrylate) based resins; TEGDMA (triethylene glycol dimethacrylate) based resins; HEMA (2-hydroxyethyl methacrylate) based resins; PMDM (pryomellitic acid diethylmethacrylate) based resins; PMGDM (pyromellitic acid glycerol dimethacrylate)

based resins; UDMA (urethane dimethacrylate) based resins; methacrylate based resins; dimethacrylate based resins; hydrophobic resins; hydrophilic resins; and hardenable monomers suitable for dental applications.

Generally, oil-based resins are not soluble in water or have limited solubility in water such that less than about 2.0% by weight of the resin dissolves when placed in water. There are many types of oil-based resins that are suitable for the present disclosure. Specific examples of acrylic resins include, but are not limited to:

Poly(acrylonitrile-co-vinylidene chloride-co-methyl methacrylate)

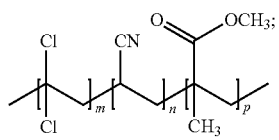

Poly(benzyl methacrylate)

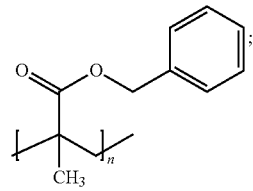

Poly(butyl methacrylate)

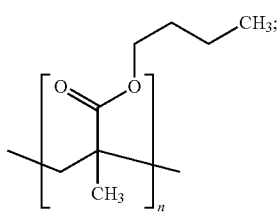

Poly(tert-butyl methacrylate)

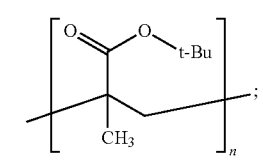

Poly(butyl methacrylate-co-isobutyl methacrylate)

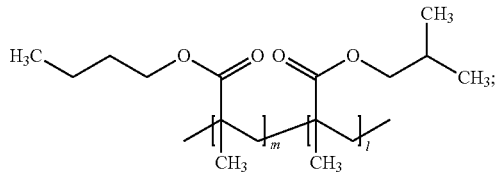

Poly(butyl methacrylate-co-methyl methacrylate)

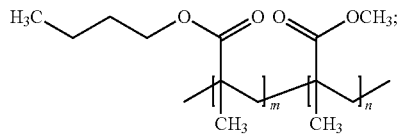

Poly(cyclohexyl methacrylate)

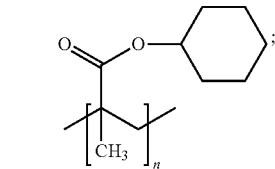

Poly[(2-ethyldimethylammonioethyl methacrylate ethyl sulfate)-co-(1-vinylpyrrolidone)]:

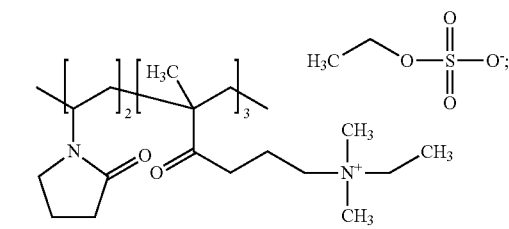

Poly(ethylene-co-glycidyl methacrylate)

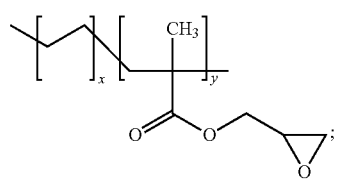

Poly(lauryl methacrylate-co-ethylene glycol dimethacrylate)

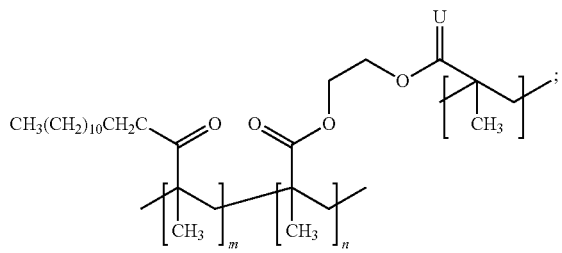

Poly(octadecyl methacrylate)

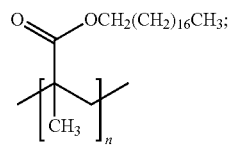

and

Poly(1-vinylpyrrolidone-co-2-dimethylaminoethyl methacrylate)

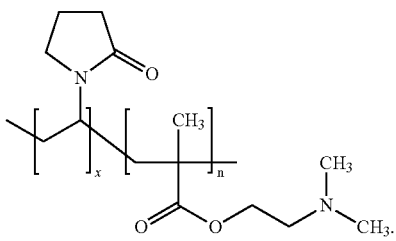

Curing

A person of ordinary skill in the art will also recognize that various methods may be used to cure resins in the present disclosure. Desirably, the curing occurs in situ in the presence of one or more metal containing materials in order to form polymeric materials with metallic nanoparticles.

In some embodiments, curing occurs by treating a resin with a chemical (i.e., chemical curing). In more specific embodiments, the resin is treated with one or more initiators, desirably in the presence of one or more metal containing materials. Non-limiting examples of suitable initiators include benzoyl peroxide (BPO), dimethylparatoluidine (DMPT), allyl thiourea (T), and cumene hydroperoxide (CH).

Initiators may be used at various concentrations and ratios for chemical curing. For instance, in some specific embodiments, chemical curing may consist of treating resins with allyl thiourea (T) and cumene hydroperoxide (CH). In other embodiments, chemical curing may consist of treating resins with benzoyl peroxide (BPO) and dimethylparatoluidine (DMPT). The above-mentioned embodiments will be described in more detail in the Examples listed below.

In other embodiments, curing can occur by treating resins with a light source, such as ultraviolet light (i.e., light curing). However, as described in detail in the Examples below, Applicants have unexpectedly observed that chemically-cured polymeric materials released more silver ions in vitro as compared to light-cured polymeric materials. Hence, at least in some embodiments, chemical curing may lead to the production of more effective antimicrobial polymeric materials.

In other embodiments, curing may entail both light curing and chemical curing. Other methods of curing resins can also be envisioned by a person of ordinary skill in the art.

Applications

A person of ordinary skill in the art will recognize that the methods of the present disclosure can be used in various embodiments to form numerous anti-microbial polymeric materials for numerous purposes. For instance, in some embodiments, the methods of the present disclosure can be used to generate polymeric materials with silver nanoparticles (AgNP) by curing PMMA in the presence of silver borate (AgB).

Desirably, the methods of the present disclosure occur in situ. Applicants envision that curing resin compositions in situ can lead to more effective polymerization, thereby producing more effective antimicrobial compositions.

More desirably, the anti-microbial polymeric materials of the present disclosure are formed in a single step. Desirably, the anti-microbial polymeric materials of the present disclosure may be formed by using environmentally-friendly chemicals.

The anti-microbial polymeric materials of the present disclosure can also have various embodiments. For instance, the anti-microbial polymeric materials of the present disclosure may be used as part of medical devices, such as dental devices. A person of ordinary skill in the art can also envision other applications.

As such, herein disclosed are at least: antimicrobial polymeric materials as herein disclosed; antimicrobial medical devices as herein disclosed; processes for forming antimicrobial polymeric materials as herein disclosed; processes for forming nanoparticles in a polymeric material(s) as herein disclosed; antimicrobial polymeric materials comprising a chemically-cured and/or dual-cured acrylic resin with in situ generated metallic nanoparticles; and, processes for forming an antimicrobial polymeric material comprising in situ generated metallic nanoparticles from a chemically-cured or dual-cured acrylic resin as herein disclosed.

From the above disclosure, a person of ordinary skill in the art will recognize that the present invention has numerous embodiments and applications. Reference will now be made to more specific embodiments of the present invention. However, Applicants note that the disclosure below is for exemplary purposes only and is not intended to limit the scope of the claimed invention in any way.

WORKING EXAMPLES

Example 1

Objective: To develop a broad-spectrum, long-lasting, antimicrobial resin loaded with in situ-generated silver nanoparticles suitable for dental and medical applications.

Materials and Methods:

Silver nanoparticles (AgNPs) were formed in situ in anti-microbial resins by adding Ag Benzoate. Next, the effect of Ag Benzoate concentration and curing method (light-curing vs. chemical-curing) on the degree of cure, nanoparticle size and formation, in vitro release of Ag ions, and in vitro antibacterial activity were determined. Transmission electron microscopy (TEM) was used to observe AgNPs. UV/Vis spectroscopy was used to further determine the presence of AgNPs, clusters of AgNPs, and release of Ag ions. Rockwell$_{15T}$ hardness was used to measure degree of cure. In addition, in vitro antibacterial assays were done to determine antimicrobial activity of these novel resins.

Synthesis of AgNP-Loaded Resins

Light-cured (LC) samples were made by dissolving different concentrations (0, 0.002, 0.02, 0.1, 0.15 and 0.2% w/w of total monomer) of Ag benzoate (Sigma-Aldrich) in dimethylaminoethyl methacrylate (DMAEMA; 2% w/w of total monomer; Sigma-Aldrich), camphorquinone (CQ: 1% w/w of monomer blend; Sigma-Aldrich), and GTE (combination of 37.5% Bisphenol A glycidyl methacrylate (Bis-GMA), 25.0% Tetraethyleneglycol dimethacrylate (TEGMA) and 37.5% Bisphenol A ethoxylate dimethacrylate (Bis-EMA)). The sample was then poured into a mold between two glass slides and light-cured on each side for 40 seconds using a Demetron Optilux 401 UV curing light gun.

Chemically-cured (CC) samples were made by dissolving different concentrations (0, 0.002, 0.02, 0.2 and 0.5%) of Ag benzoate concentrations into 2% DMAEMA and then into liquid orthodontic monomer (Dentsply). The samples were then mixed with PMMA powder following the manufacturer's guidelines. This PMMA-based resin blend was immediately poured into molds between two glass slides and allowed to chemically cure.

Rockwell Hardness

The hardness of cured samples was measured with a Rockwell hardness tester with a 15T ¹⁄₁₆" ballpoint indenter with a 15 Kg force. Three measurements were made on different areas of each of the samples to verify that the samples cured evenly.

Transmission Electron Microscopy

Cured samples were cut into 100 nm thin slices using a microtome, placed on Cu grids, and observed using Transmission electron microscopy (Jeol JEM-1230 transmission electron microscope).

Ultraviolet-Visible Spectroscopy

Samples were also cured in plastic cuvettes and UV/Vis spectra from 200-800 nm were taken (SmartSpec 3000 spectrophotometer, Bio-Rad) using the control (0% Ag benzoate) as a blank.

For chemically-cured (CC) samples, an uncured control sample with 0% Ag benzoate was used as the blank for 0 min and a 60 min cured control sample with 0% Ag benzoate was used as the blank for 60 min samples to ensure that any absorbance due to the resin is properly accounted for.

In Vitro Ag Release Study

Samples were placed into glass vials with 5 mL of sterile deionized water (n=3). At certain intervals (one day, four days, one week, two weeks, one month) 1 mL of the water was extracted and a UV/Vis spectra from 200-800 nm was recorded. The control samples contained 0% Ag benzoate. The UV/Vis scan of the control was taken using sterile deionized water as the blank while the readings for all the other samples were taken using the control as the blank. At each time period, the water was replaced to maintain sink conditions.

Inhibitory Effects of AgNP-Loaded Resin Discs on the Growth of S. mutans

Based on the in vitro release data and a pilot growth inhibition assay showing minimal effect from the 0.2% Ag benzoate LC samples (data not shown), the growth inhibition assay was only done with CC resins made with 0 (negative control), 0.2 and 0.5% Ag benzoate. S. mutans (TACC 25175) was grown on TSBY (Trypticase Soy Broth with 0.5% yeast extract) agar plates in an anaerobic chamber with a mixed gas ($N_2$=85%, $H_2$=5, and $CO_2$=10%) and samples were placed on the bacteria-containing agar and anaerobically inoculated at 37° C. for 5 days to determine their efficacy in inhibiting bacterial growth by identifying any zones of inhibition.

To estimate colony formation, 20 μl of different concentrations of the bacteria (about $10^{-1}$, $10^{-2}$, $10^{-3}$, 10', $10^{-5}$ and $10^{-6}$/ml) were homogenously spread onto each area of the surface on the gelled TSBY agar plates with a sterile spreader. The colony formation was determined by countable colonies counted from suitable dilution for each sample.

Results

Synthesis of AgNP-Loaded Resins

The higher the Ag benzoate concentration, the more difficult there was to cure the samples. The highest Ag benzoate concentration that could be incorporated and light-cured was 0.2% w/w. However, for chemically cured samples, samples with as much as 0.6% w/w Ag benzoate were curable.

Figure 2:
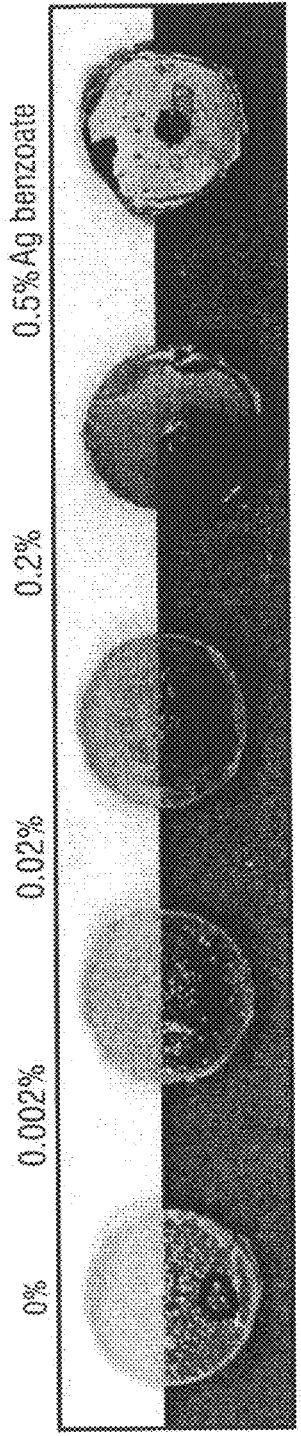
FIG. 2 illustrates photographs of chemically-cured (CC) samples with different Ag benzoate concentrations.

FIGS. 1 and 2 show that, as the Ag benzoate concentration increased, the amber color of the samples, due to the plasmon effect of the AgNPs, became darker. Also the chemically cured samples shown in FIG. 2 were lighter in color than the light-cured samples shown in FIG. 1 at the same Ag benzoate concentration.

Rockwell Hardness

Figure 3:
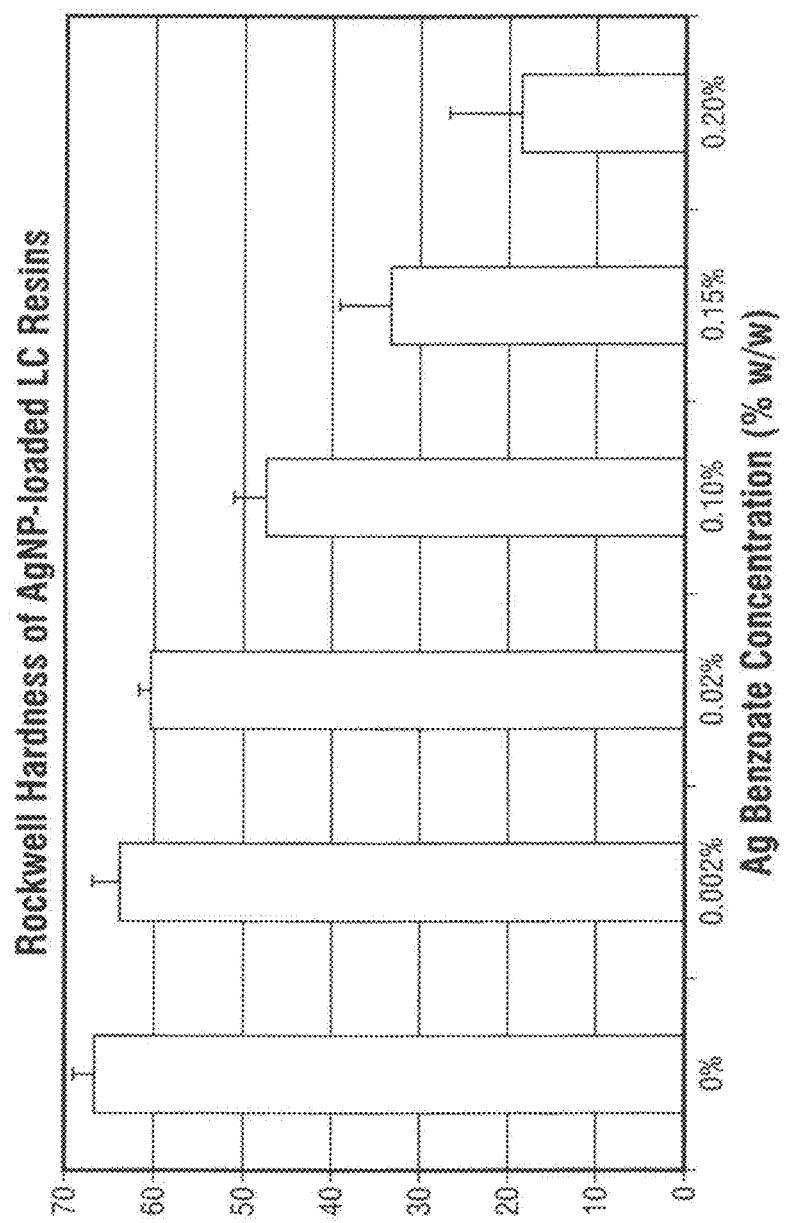
FIG. 3 illustrates Rockwell$_{15T}$ Hardness of light-cured samples made with different concentrations of Ag benzoate.
Figure 4:
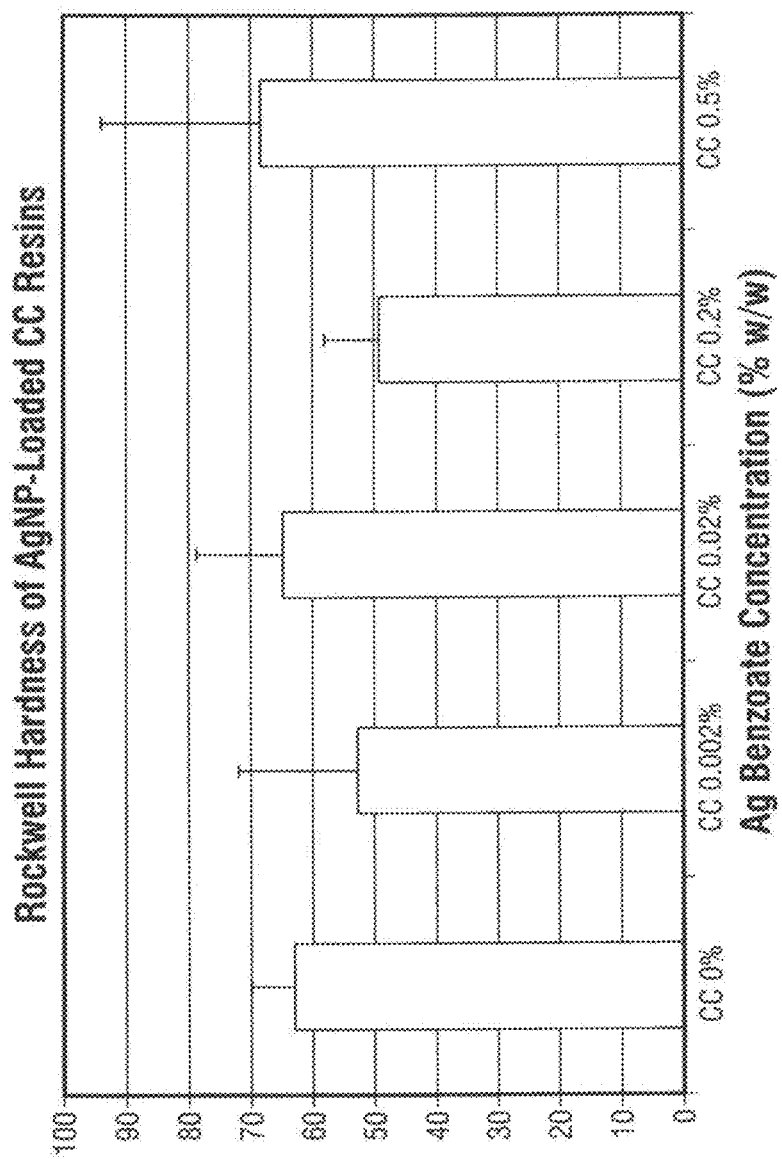
FIG. 4 illustrates Rockwell$_{15T}$ Hardness of chemically-cured samples made with different concentrations of Ag benzoate.
Figure 5B:
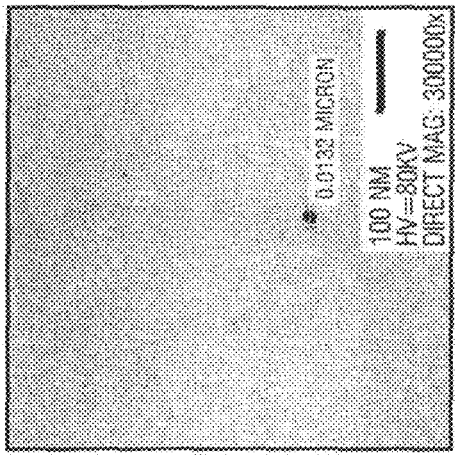
FIG. 5 illustrates transmission electron micrographs of light-cured samples with different Ag benzoate concentrations (A: 0% negative control, B: 0.002% Ag benzoate, C, 0.02% Ag benzoate, D: 0.1% Ag benzoate, E: 0.15% Ag benzoate, F: 0.2% Ag benzoate). Bar is 100 nm.
FIGS. 5a and f were taken at 80,000× and the rest were taken at 300,000×.
Figure 5C:
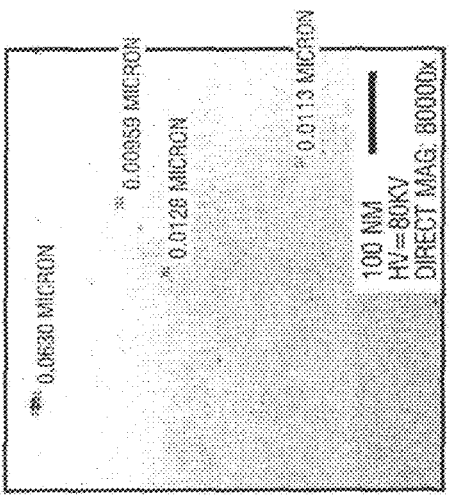
Figure 5A:
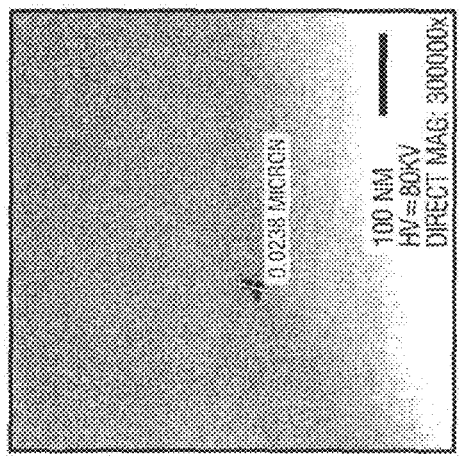
Figure 5D:
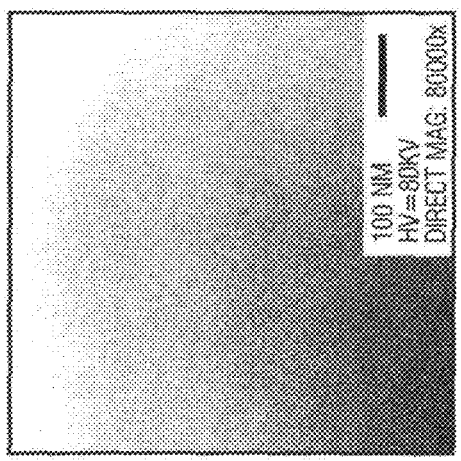
Figure 5E:
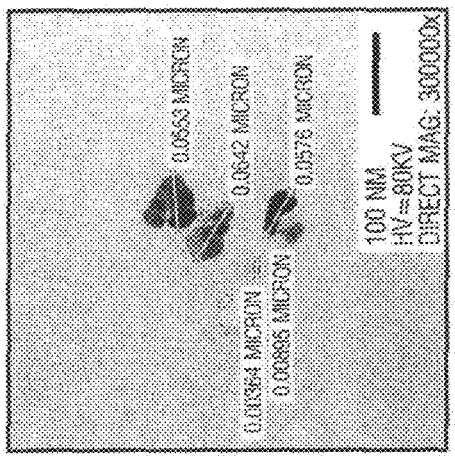
Figure 5F:
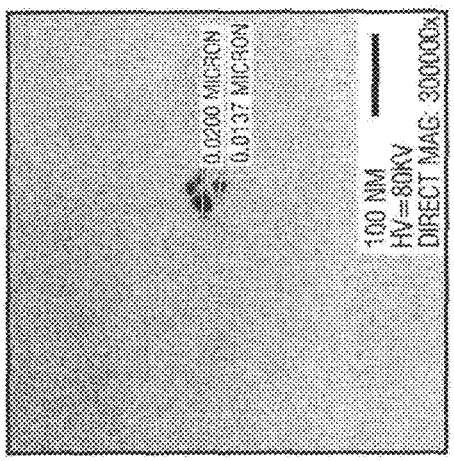
Figure 6A:
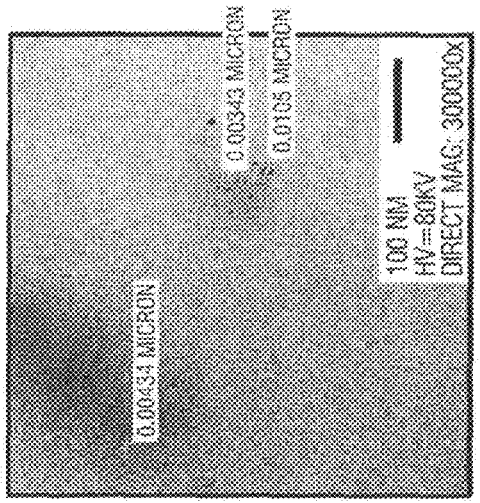
FIG. 6 illustrates transmission electron micrographs of chemically-cured samples with different Ag benzoate concentrations (A: 0.002% Ag benzoate, B: 0.02% Ag benzoate, C, 0.2% Ag benzoate, D: 0.5% Ag benzoate). Bar is 100 nm. All FIGS. were taken at 300,000×.
Figure 6B:
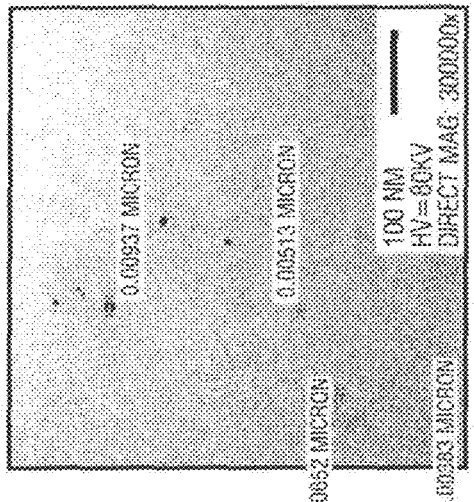
Figure 6C:
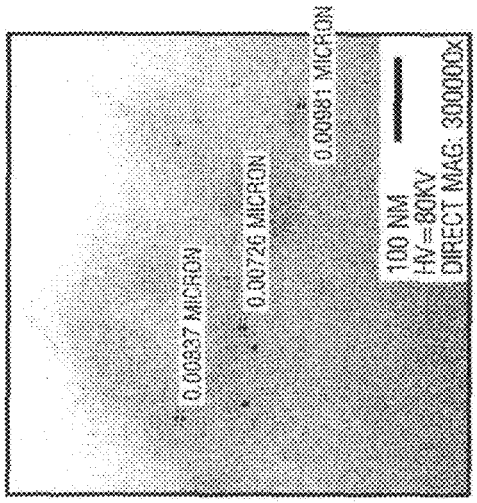
Figure 6D:
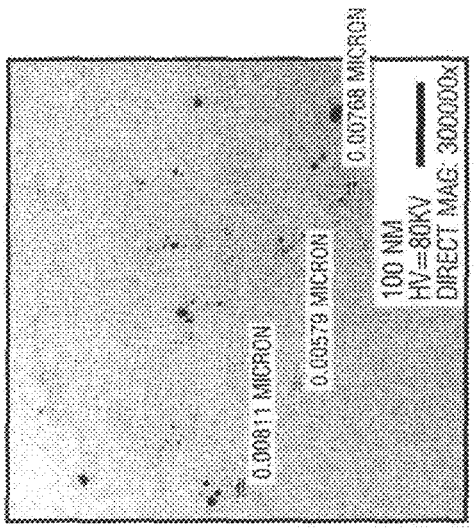

FIG. 3 shows that Rockwell hardness of LC samples decreased significantly when Ag benzoate concentrations increased above 0.1% w/w. Above 0.2%, the samples did not cure well and were very soft. However, FIG. 4 shows that the hardness of CC samples did not change significantly from the 0% control, but this was mainly due to the large standard deviations caused by pores that are formed in the mixing process of the different components of the chemical cure resin.

Transmission Electron Microscopy

TEM images shown in FIGS. 5a-5f illustrate that there are sparse individual particles and large nanoparticle clusters in the LC samples. The higher the Ag benzoate concentration, the more the number of nanoparticles, and the larger the nanoparticle clusters. Some clusters were as large as 50-70 nm. Nanoparticles were generally between 10-20 nm, but with the 0.2% samples, there were also many smaller particles.

However, equivalent TEM images of the CC samples shown in FIGS. 6a-6f indicate that there were distinctly more nanoparticles that were distributed more widely. In addition, there were not as many nanoparticle clusters.

The individual particles from all samples shown in FIGS. 5 and 6 usually ranged from about 2 nm to about 18 nm in size. However, it is apparent that the CC samples had smaller nanoparticles. This might explain why the amber color of the CC resins was lighter than that of the LC samples. Finally, as the Ag benzoate concentration increased, so did the number of visible nanoparticles.

The TEM images shown in FIGS. 5 and 6 represented samples with the following Ag benzoate concentrations: FIG. 5a: 0% (negative control), FIG. 5b: 0.002%; FIG. 5c: 0.02%; FIG. 5d: 0.1%; FIG. 5e: 0.15%; FIG. 5f: 0.2%; FIG. 6a: 0.002%; FIG. 6b: 0.02%; FIG. 6c: 0.2%; FIG. 6d: 0.5%. The Bar shown in FIGS. 5 and 6 is 100 nm. FIGS. 5a and f were taken at 80,000×. The rest of the images were taken at 300,000×. Samples containing greater than 0.2% Ag benzoate could not be fully cured.

Ultraviolet-Visible Spectroscopy

Figure 7:
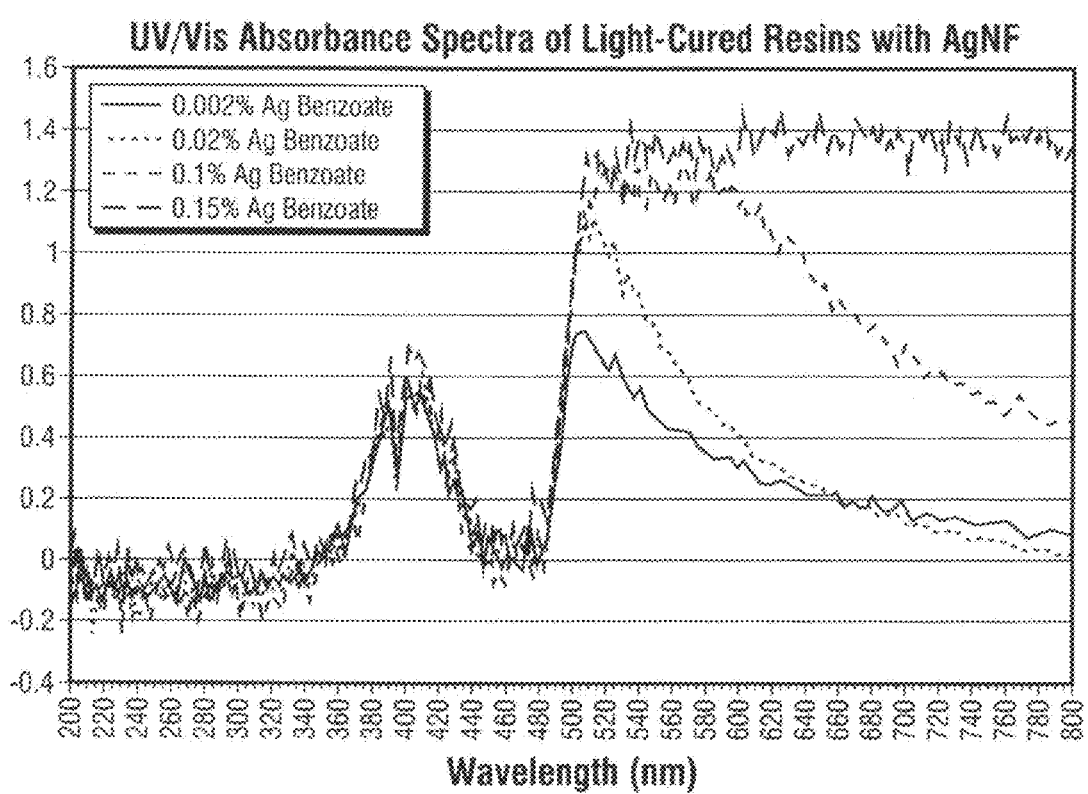
FIG. 7 illustrates UV/visible light spectra of light-cured resins cured with different concentrations of Ag benzoate. Characteristic peak of silver nanoparticles (AgNPs) at 400 nm and the broader peak beginning at 500 nm may be due to nanoparticle clusters.

It is known that spherical AgNPs have a peak centered around 400 nm. All the LC samples showed a peak centered around 400 nm (FIG. 7). However, there was also a peak starting at 500 nm and continuing onto 800 nm that consistently got broader as the Ag benzoate concentration increased. Without being bound by theory, Applicants envision that this may be due to the formation of Ag nanoclusters.

Figure 8:
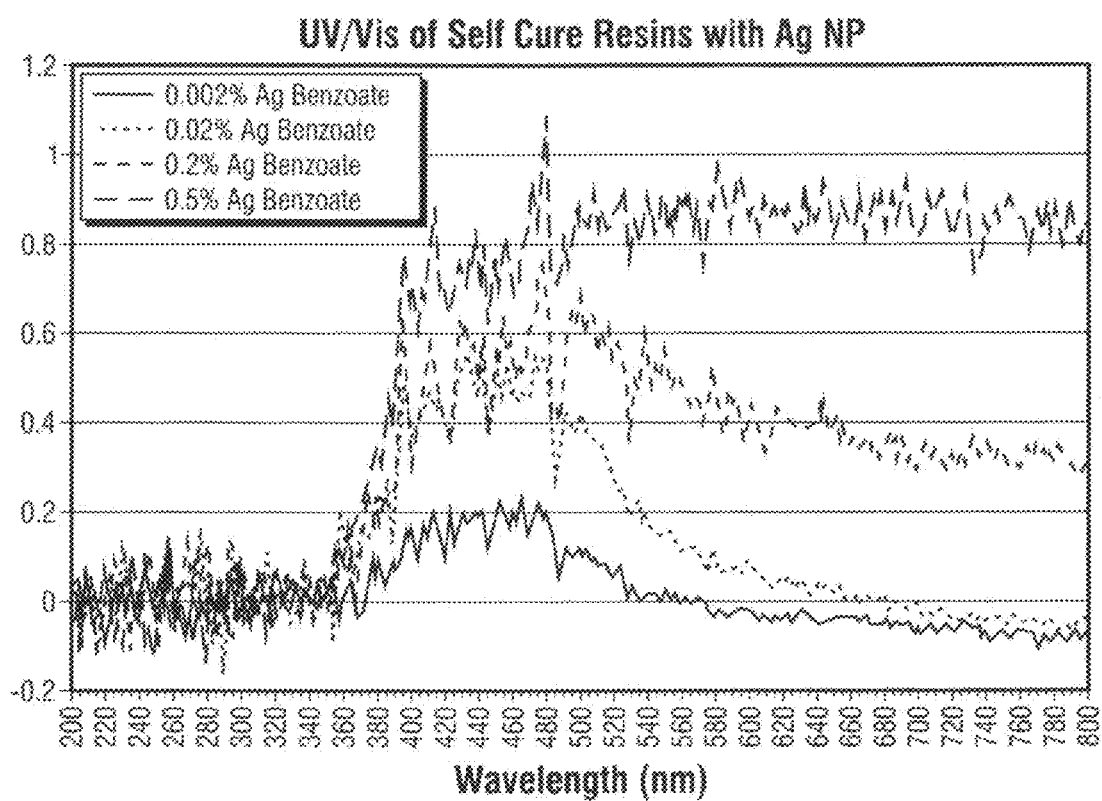
FIG. 8 illustrates UV/visible light spectra of chemically-cured resins cured with different concentrations of Ag benzoate.

The UV-Vis spectra for the CC samples show a peak centered around 450 nm (FIG. 8). As the Ag benzoate concentration increased, the broad peak beginning at around 500 nm became visible. This broad peak also became visible after 24 hours for most of the samples as more NPs were formed. However, unlike the two distinct peaks in the LC samples, the peaks in the CC samples were diffused. In addition, the peaks in the CC samples overlapped with the peak at 450 nm.

a.

In Vitro Ag Release Study

Figure 9:
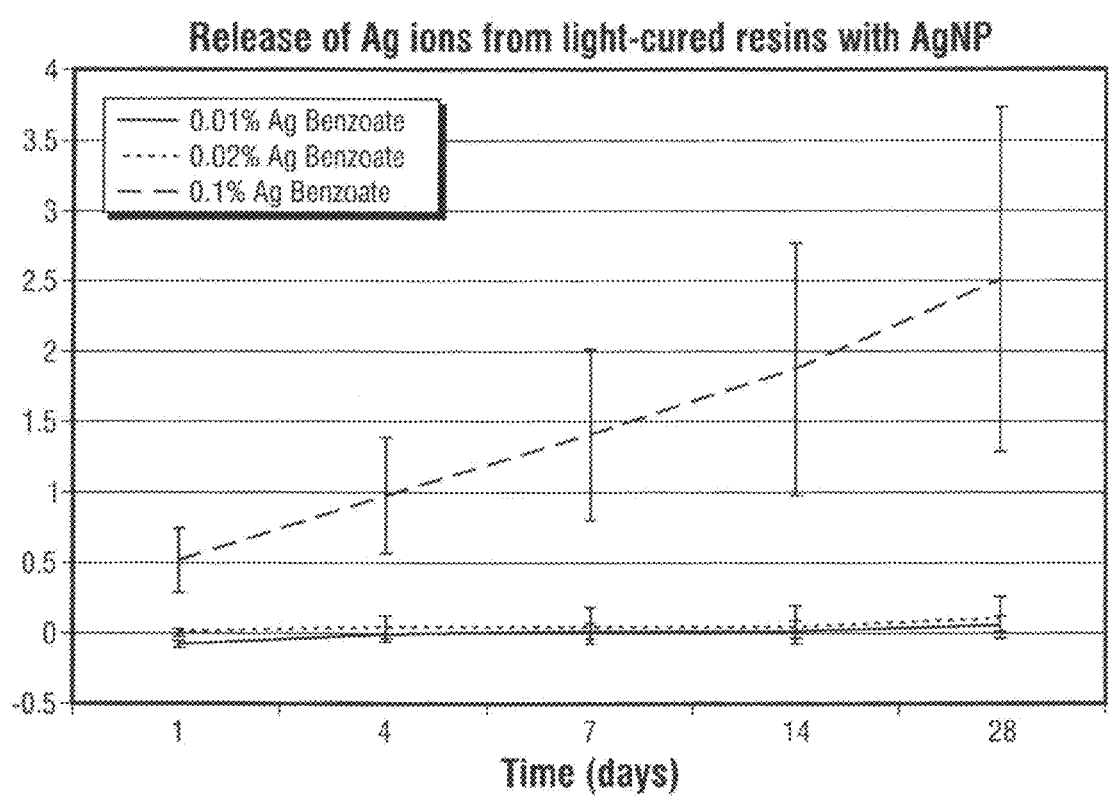
FIG. 9 illustrates UV absorbance at 223 nm versus time showing cumulative Ag ion release from light-cured resins made with different concentrations of Ag benzoate.
Figure 10:
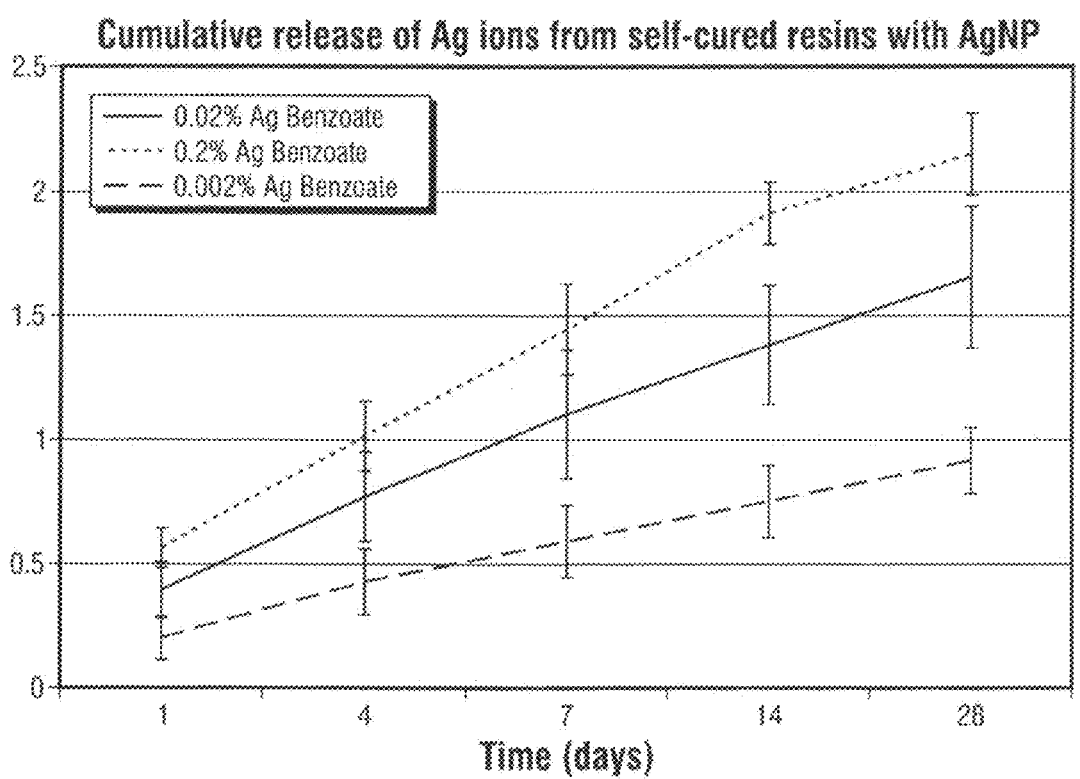
FIG. 10 illustrates UV absorbance at 223 nm versus time showing cumulative Ag ion release from chemically-cured resins made with different concentrations of Ag benzoate.

FIGS. 9 and 10 show the UV/Vis absorbance measuring the released Ag ions in water versus time. Peaks characteristic of Ag ions in water are centered around 223 nm. For LC samples, there was no detectable release of Ag ions until Ag benzoate concentration reached 0.1% (FIG. 9). However for CC samples, Ag ion release was detected for all concentrations, and as the Ag benzoate concentration increased the peak became more intense (FIG. 10). However, over time the Ag ion release gradually decreased.

Inhibitory effects of AgNP-loaded resin discs on the growth of S. mutans

Figure 11A:
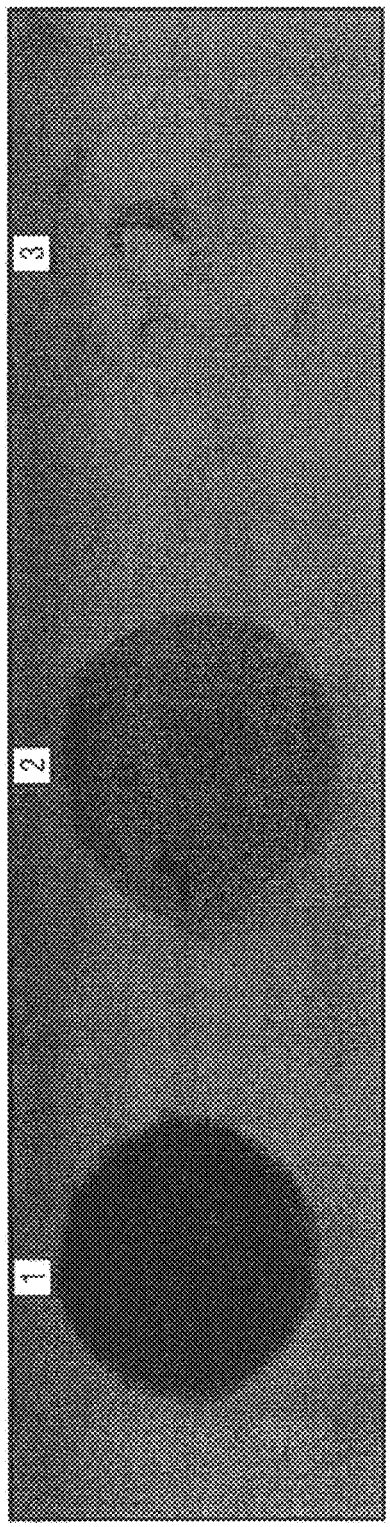
FIG. 11 illustrates inhibitory effect of a chemically-cured resin disk containing AgNP on the growth of *Streptococcus mutans*. Panel A shows the resin samples, and panel B shows the agar with the samples removed (A1: Resin made with 0.5% Ag benzoate; A2: Resin made with 0.2% Ag benzoate; A3: Resin made with 0% Ag benzoate (negative control)). B1 shows a transparent ring suggesting growth of *S. mutans* was inhibited. B2 shows a semi-transparent ring demonstrating partial inhibition. In contrast, B3 shows normal bacterial growth.
Figure 11B:
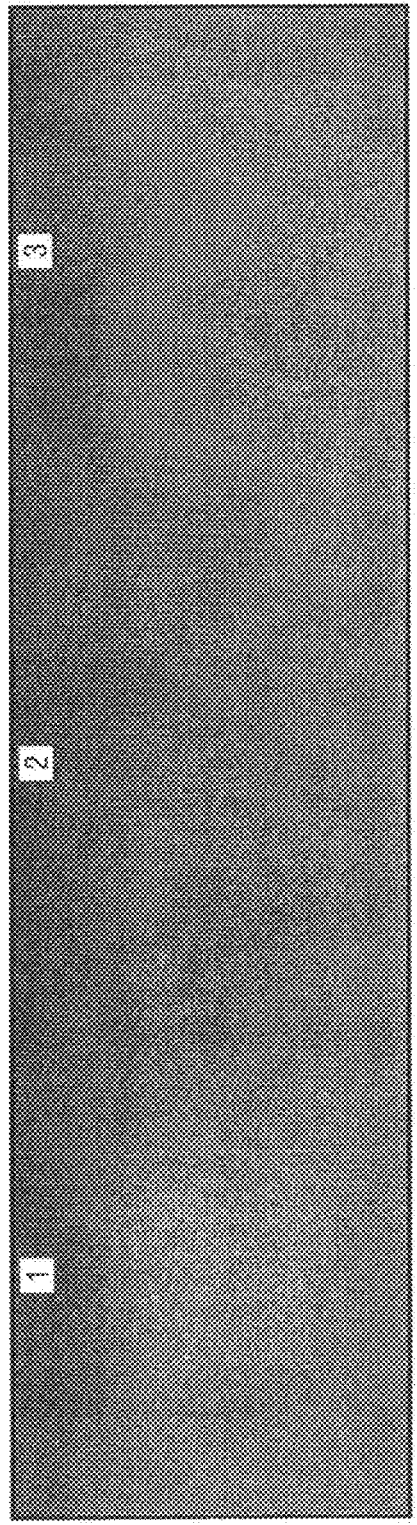

FIG. 11A shows the presence of the CC disks on agar. FIG. 11B shows the agar with the resin discs removed after 5 days of incubation at 37° C. A clear zone of inhibition is clear in A1 and B1, where resins with 0.5% Ag benzoate were used. A2 and B2 show a vague zone where resins made with 0.2% Ag benzoate were used. A3 and B3 show no zones of inhibition when Ag benzoate was not used.

Figure 12:
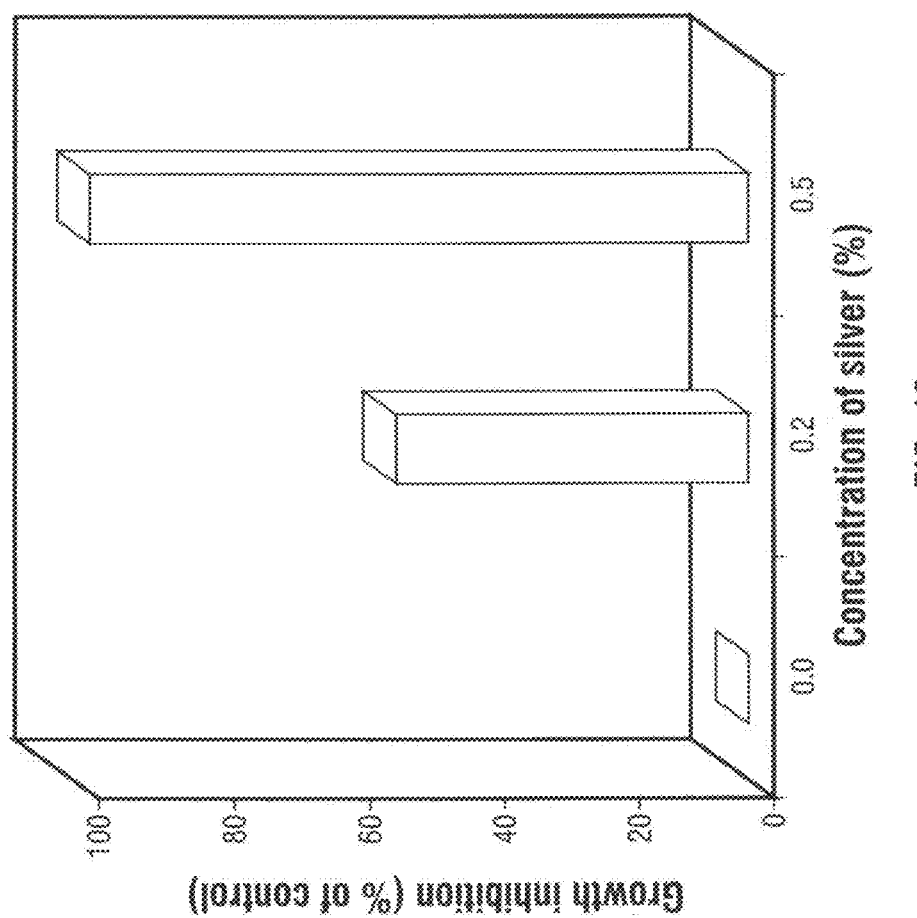
FIG. 12 illustrates growth inhibition of *S. mutans* by chemically-cured resin disk containing AgNP. Resin containing 0.5% Ag benzoate showed 97.5% inhibition of the growth of *S. mutans*, as compared to 0% inhibition in the negative controls. Resins made with 0.2% Ag benzoate inhibited 52.4% bacterial growth.

FIG. 12 shows the inhibition of the growth of S. mutans by AgNP-loaded CC resins. Resins made with 0.5% Ag benzoate showed 97.5% inhibition and those made with 0.2% Ag benzoate inhibited 52.4% of S. mutans growth as compared to 0% negative controls. The results demonstrate that 0.5% silver containing resin inhibited almost all of the bacterial growth. Even resins containing 0.2% silver significantly inhibited bacterial growth.

Hardness tests showed that in light cured samples, as the concentration of Ag benzoate increased the degree of cure decreased. Because silver ions are reduced to silver atom clusters and nanoparticles, it is interfering with the free radical polymerization process. Thus, the more silver there is, the more it is interfering with the curing process. However, it is interesting that this did not seem to affect the degree of cure for chemically-cured samples to the same degree and while the maximum concentration of silver benzoate that light-cured resins could cure with was 0.2%, it was 0.6% for the chemically-cured resins. It is also interesting that the color of light-cured samples were darker for the same Ag benzoate concentration and it may be due to the larger particle sizes that were seen with TEM. It seems that the slower chemical curing process is allowing more nucleation sites for Ag NPs to form, generating more particles, a better dispersion of the particles and smaller particle sizes.

The UV-Vis spectra of the resins further supported the TEM data in that spherical particles were identified as AgNPs since the single peak around 400 nm is characteristic of spherical AgNPs. The narrower peaks of the LC resins also support TEM observations that the particles are larger than those formed by CC resins. The broader peaks that begin after 500 nm but are not as visible in the CC resins also support the TEM data in that there seems to be more clustering of the NPs in the LC samples.

The release study showed that continued release of silver ions was only detected with at least 0.1% Ag benzoate LC samples, while CC samples showed release with even 0.002% Ag benzoate samples. The 0.1% LC sample may have released silver ions only because of a visible crack since 0.15% LC samples did not release any Ag ions (data not shown). The release of Ag ions from CC samples may be due to the smaller particle size and more homogeneous distribution of the NPs and/or the higher porosity and reduced hardness that exist in CC samples as compared to LC samples.

Only the 0.2% and 0.5% Ag benzoate CC samples (with the most silver ion release) were tested in the in vitro bacterial growth inhibition assay, a clear zone of inhibition of S. mutans is visible for the 0.5% and slightly visible for the 0.2% samples. This correlated to a 97.5% and 52.4% inhibition of S. mutans growth.

Example 2

Objective: Optimize resin initiator and Ag-generating components in order to generate AgNP-loaded resins that have comparable degrees of cure and mechanical properties as non-loaded resins with allyl thiourea (T) and hydroperoxide (CH).

Background: The effect of low-color initiator system using cumene hydroperoxide (CH) and allyl thiourea (T) on hardness (as a measure of degree of cure) of cured antimicrobial resins has been determined. However, due to interference with the silver (Ag) microelectrode and UV/Vis readings, we have changed the initiator system to benzoyl peroxide and dimethyl-paratoluidine (BPO/DMPT).

Material hardness and mechanical properties can be increased by increasing initiator concentration. However, that increased initiator concentrations decreased Ag release rates. Antimicrobial studies show that with 1% Ag benzoate, we are now able to produce very clear rings of inhibition, which was not possible previously. The 1.0BP0:0.8DMPT formulation produced specimen that inhibited bacteria the most while the 1.6BPO:1.6DMPT formulation produced the strongest specimen.

AgNPs were formed in situ in Bis-GMA based antimicrobial resin by dissolving Ag benzoate (AgB) (0.5 w/w resin) into dimethylaminoethyl methacrylate (DMAEMA; 2% w/w resin) and dissolving that into the monomer before curing. Applicants also varied the concentrations of their self-cure initiator components, allyl thiourea (T) and cumene hydroperoxide (CH) (T=2-10% and CH=4-20 wt. %).

Disc-shaped specimens ⅜" in diameter and ¹⁄₁₆" thick (n=5) were made and used to evaluate degree of cure using Durometer hardness 24 hours post cure.

Figure 13:
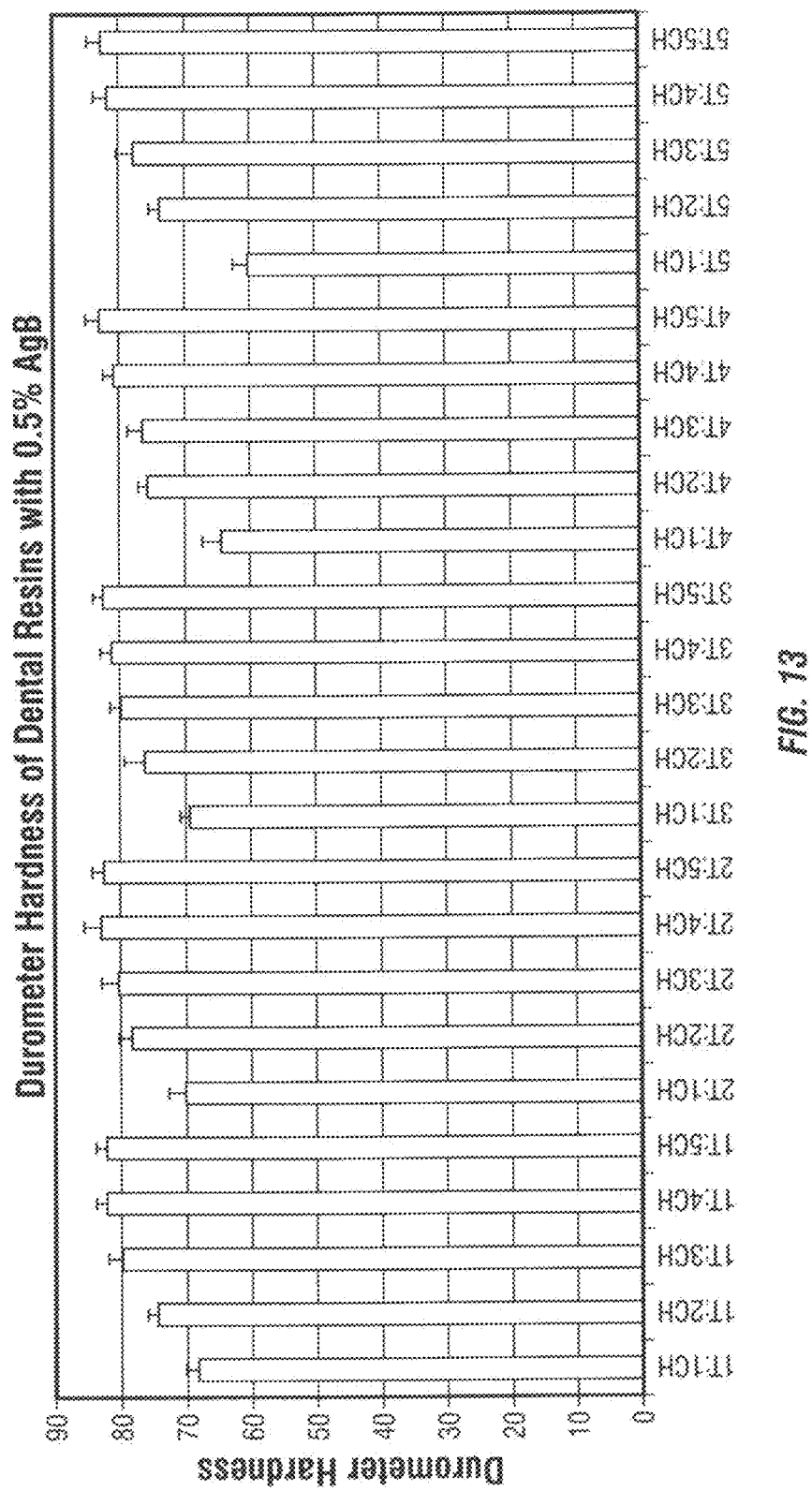
FIG. 13 illustrates the durometer hardness of anti-microbial resins with 0.5% AgB. The resins were cured with initiator systems that contained various ratios of allyl thiourea (T) and cumene hydroperoxide (CH) (T/CH systems)

FIG. 13 shows Durometer Hardness of the samples with varying amounts of T and CH and 0.5% AgB. As T and CH concentration increased, hardness and degree of cure also increased. However, above a certain concentration (greater than 3T and 4 CH), there was no added benefit. In fact, there was a decrease in hardness with too much T. Nonetheless, the highest hardness values were over 80, which are comparable to unfilled antimicrobial resins. Thus, Applicants have successfully been able to cure resins containing AgB with the above-mentioned self-cure initiator systems.

Example 3

Objective: To determine the in vitro Ag-ion release kinetics of resins loaded with T and CH.

Methods: Another set of disc-shaped samples (n=5) with 0.5% AgB were made and immersed in water at 37° C. Next, a Ag microelectrode was used to measure Ag ion release at different time intervals up to 28 weeks (at 1 day, 3 days, 1 week, 2 weeks and 4 weeks).

Results: Applicants have not been able to accurately measure Ag ion release from this resin system using the Ag microelectrode. After extensive troubleshooting, it was determined that the T, CH and different resin components interfered with the microelectrode readings causing it to fluctuate and become inconsistent.

Alternative Approaches and Results: Applicants have tried using UV/Vis spectroscopy to measure Ag ion release, as Applicants had previously done. However, T and CH also affected this system. Thus, Applicants have changed the initiator system to the benzoyl peroxide/aromatic amine (BPO/DMPT) system, and Applicants have done some experiments to determine the usable concentrations to be between 0.8-1.6% for both BPO and DMPT. This system also interfered with the Ag ion microelectrode readings and UV/Vis readings, but Applicants were eventually able to use Atomic Absorption Spectroscopy (AAS) to measure Ag ion release. In addition, Applicants will investigate the use of 1% AgB since the BPO/DMPT initiator system seemed to cure well.

Conclusion: The T/CH self-cure initiator system is capable of curing antimicrobial resins in the presence of AgB to generate in situ AgNPs. However, in conjunction with the interference problems that Applicants encountered with the T/CH system and the Ag microelectrode in Example 3, Applicants have switched to the benzoyl peroxide/dimethyl-paratoluidine (BPO/DMPT) system for the remainder of the project.

Example 4

Objective: Optimization of resin initiator and Ag-generating components to generate AgNP-loaded resins with comparable degree of cure and mechanical properties to non-loaded resins with BPO/DMPT.

Methods: AgNPs were formed in situ in Bis-GMA based antimicrobial resin by dissolving Ag benzoate (AgB) (0.5 and 1.0% w/w resin) into dimethylaminoethyl methacrylate (DMAEMA; 2% w/w resin) and dissolving that into the monomer before curing. Applicants also varied the concentrations of benzoyl peroxide (BPO) and dimethylparatoluidine (DMPT) from 0.8 to 1.6%. The negative control group was the resins with no AgB or DMAEMA.

Disc-shaped specimens 3/8" in diameter and 1/16" thick (n=5) were made and used to evaluate degree of cure using Durometer hardness 24 hours post cure. Three-point bending tests (n=5) were conducted on bar samples (2 mm×2 mm×20 mm) and loaded to fracture on an MTS machine. The modulus and ultimate transverse strength were determined.

Figure 14:
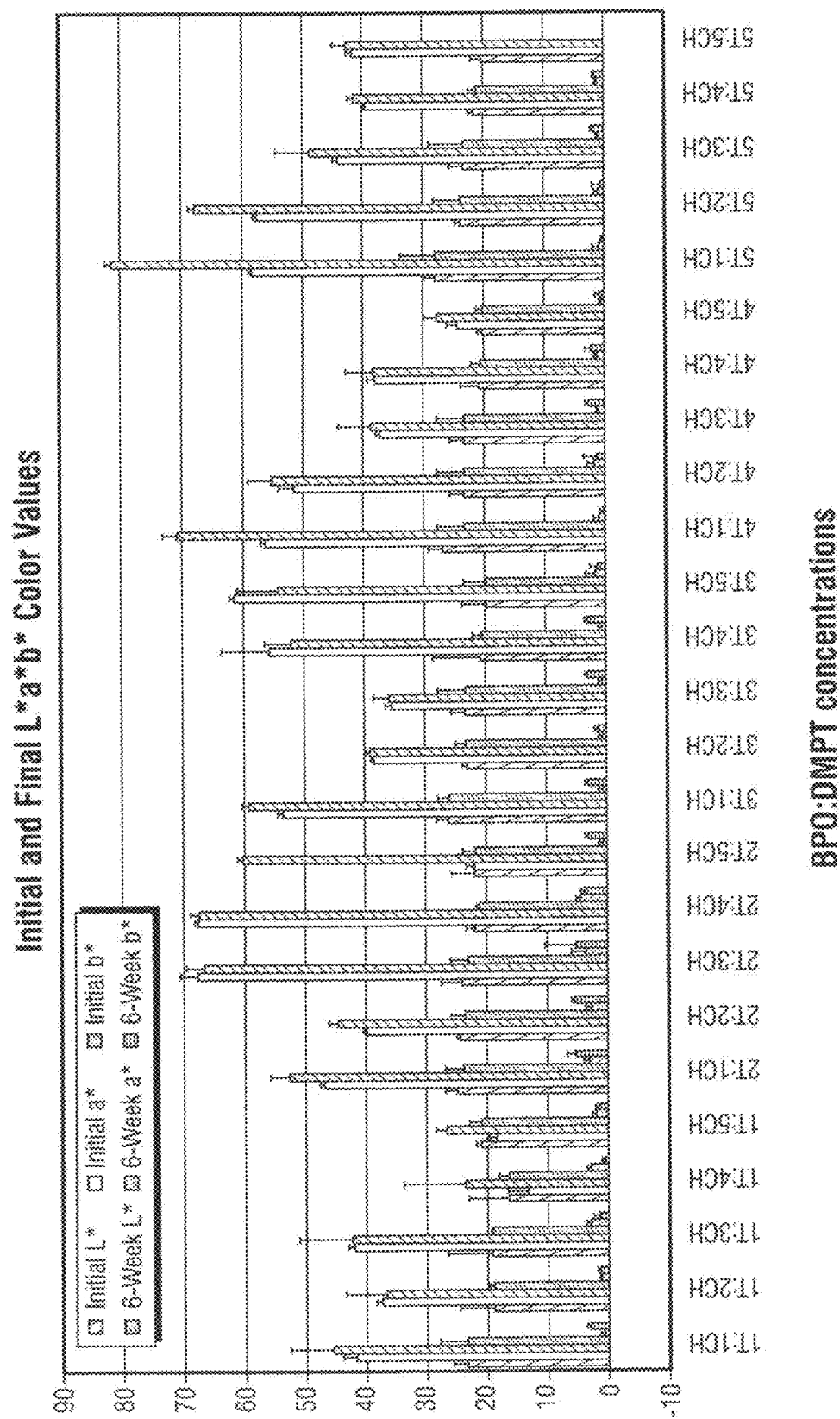
FIG. 14 illustrates the durometer hardness of anti-microbial resins with different concentration of silver benzoate (AgB). The resins were cured with initiator systems that contained various ratios of benzoyl peroxide (BPO) and dimethylparatoluidine (DMPT) (BPO/DMPT systems)

Results: FIG. 14 shows Durometer Hardness of the samples with varying amounts of BPO and DMPT and AgB. As BPO concentration increases, the effect of DMPT concentration increases. These values are generally lower than those for the T/CH system, but that may be because Applicants need to use more initiator as shown in the 1.6:1.6 formulation. Nonetheless, the highest hardness values were over 80, which are comparable to unfilled antimicrobial resins. Thus, Applicants have cured resins containing AgNP with both T/CH and BPO/DMPT initiator systems.

It needs to be noted that due to an error, the three-point bending tests for 0.8B:0.8D, 1.0B:0.8D and 0.8B:1.0D with 1% Ag were done 72 hours after initiating cure, while all the other samples were measured after 24 hours. This error gave rise to a new understanding of the system that the curing process continues past 24 hours. Thus, while the Ag-containing samples seem weaker, they actually may not be once it is given sufficient time to cure to completion. Nonetheless, Applicants assert that these experiments are preliminary and must be repeated.

Also, because there were many more T/CH formulations with higher hardness than BPO formulations, 3-point bending tests were done with the 2T:4CH formulation at 24 and 72 hours. This system proved to cure more quickly than the BPO system. In addition, the system demonstrated an increase in hardness, modulus and ultimate transverse strength. In fact, they had higher values than those of the best BPO systems without AgB. Results are shown and further described below in FIGS. 17-19. Ag release measurements with T:CH resins are currently underway using Atomic Adsorption Spectroscopy.

Figure 15:
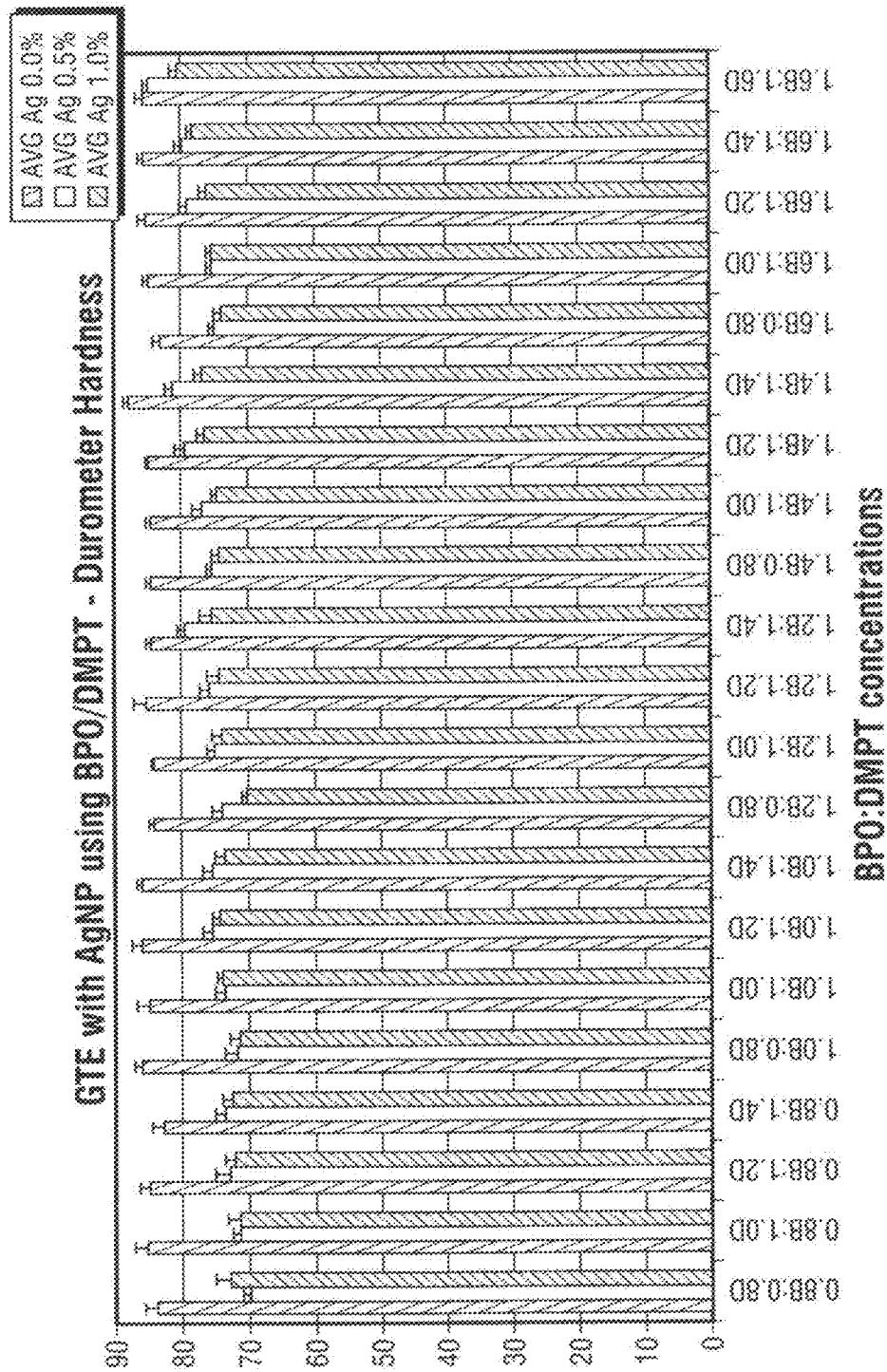
FIG. 15 illustrates the modulus from three-point bending analysis of several anti-microbial resins described in FIG. 14.
Figure 16:
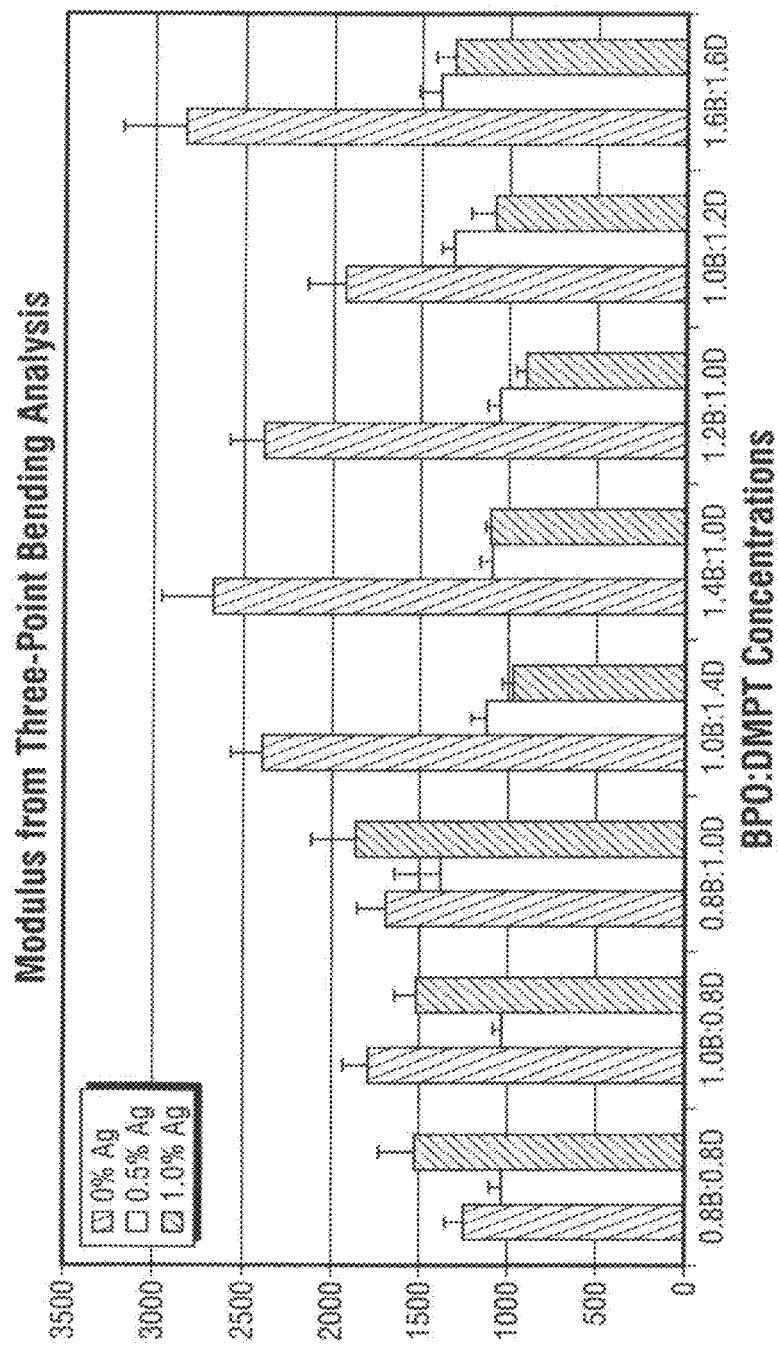
FIG. 16 illustrates the ultimate transverse strength from three-point bending analysis of several anti-microbial resins described in FIG. 14.

FIGS. 15 and 16 show the modulus and ultimate transverse strength from the three-point bending analysis. This is a smaller set of samples that were chosen based on in vitro release results in Example 3 using UV/Vis spectrophotometer to span the range of release rates.

Figure 17:
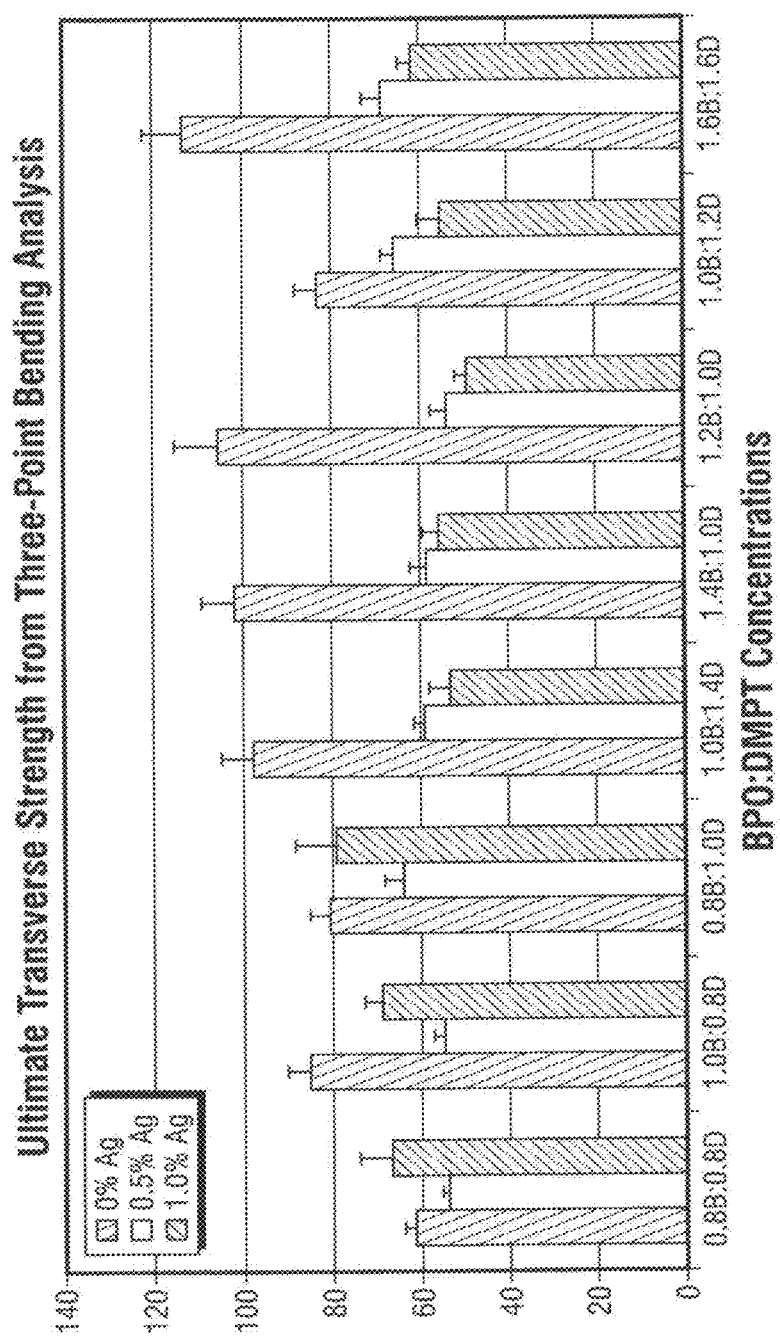
FIG. 17 illustrates the durometer hardness of anti-microbial resins that were cured with initiator systems that contained various ratios of allyl thiourea (T) and cumene hydroperoxide (CH)

FIG. 17 shows durometer hardness of Antimicrobial resins with AgB using 2T:4CH as self-cure initiator. Ag-containing resins had significantly higher hardness than controls at $p<0.05$ level. These values are comparable to unfilled commercial antimicrobial resins.

Figure 18:
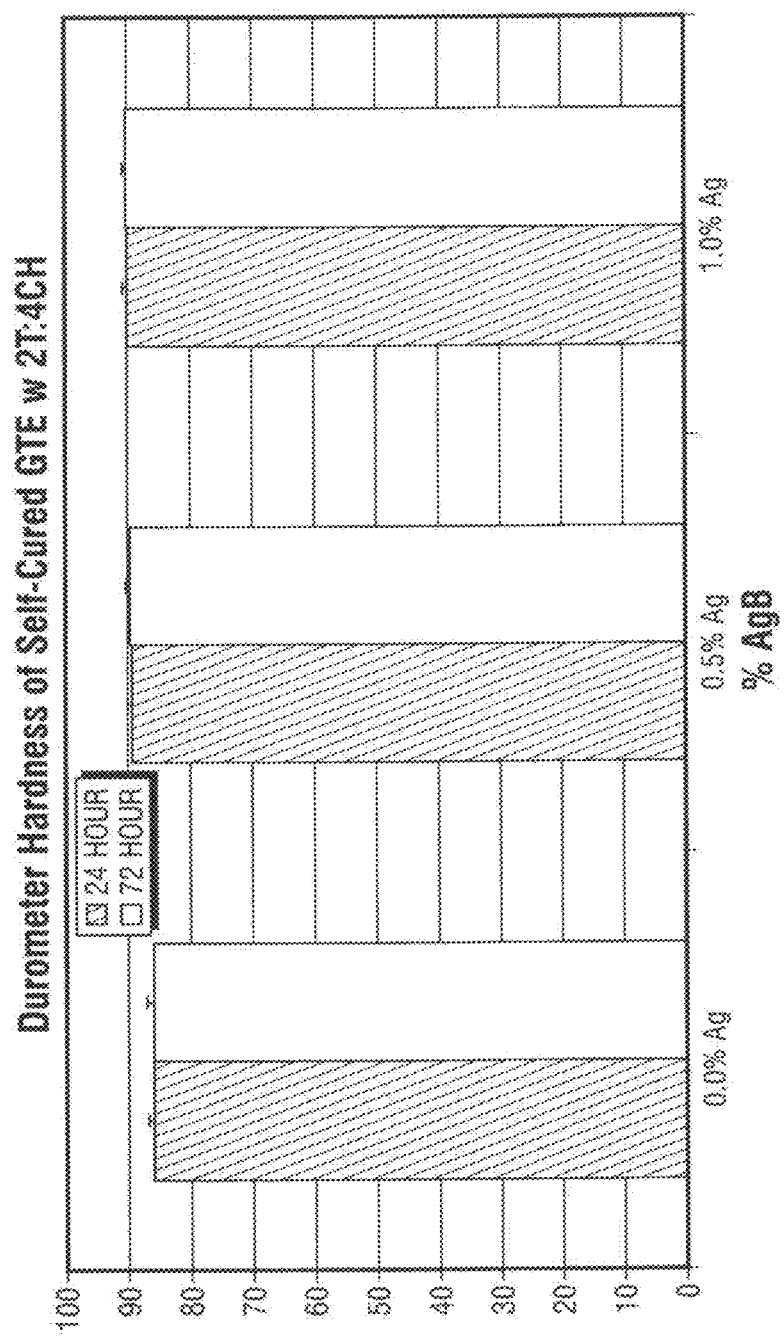
FIG. 18 illustrates the modulus of anti-microbial resins described in FIG. 17.
Figure 19:
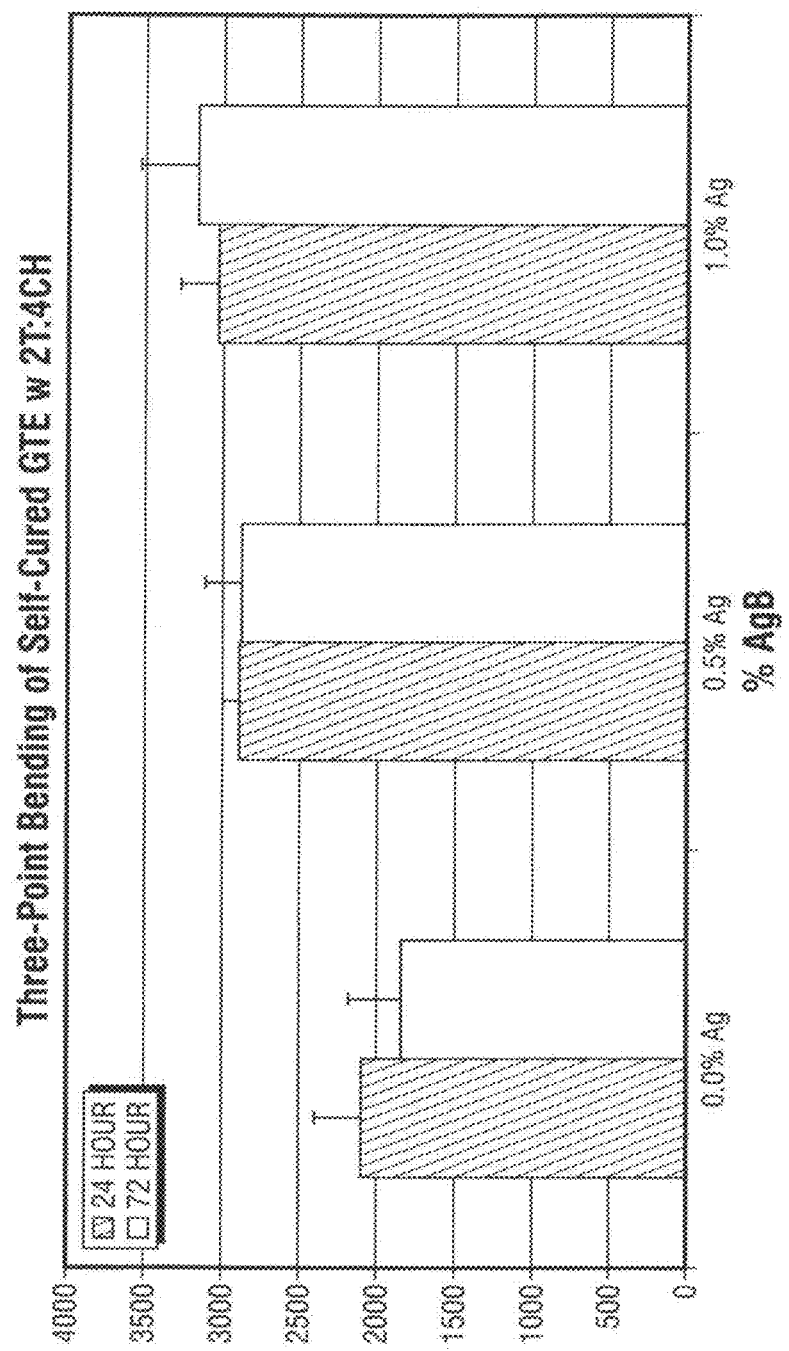
FIG. 19 illustrates the three-point bending analysis of anti-microbial resins described in FIG. 17.

FIGS. 18 and 19 show the modulus and ultimate transverse strength from the three-point bending analysis of Antimicrobial resins with AgB using 2T:4CH as self-cure initiator. Again, the Ag-containing resins had significantly increased moduli and are even higher than the best controls using BPO.

Example 5

Objective: To determine in vitro Ag-ion release kinetics of resins loaded with BPO/DMPT.

Methods: A subset of disc-shaped samples (n=5) were made and immersed in water at 37° C. and Ag ion release was measured using AAS at different time intervals up to 28 weeks (at 1 day, 3 day, 1 week, 2 weeks, and 4 weeks). This subset was chosen based on initial UV/Vis release data to cover the range of Ag release rates. This subset was also used for the three-point bending and antimicrobial tests.

Figure 20:
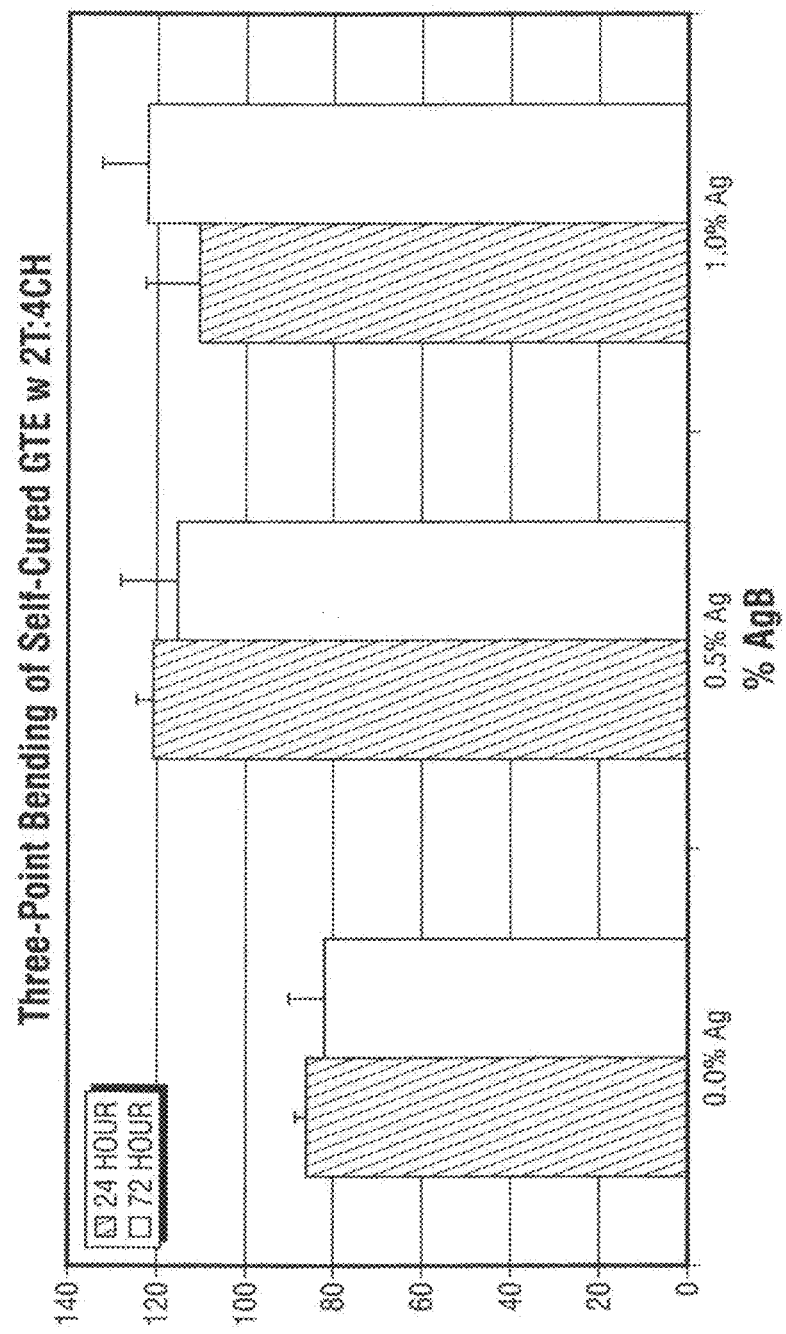
FIG. 20 illustrates in vitro Ag release studies from various anti-microbial resins with 0.5% AgB that were cured with BPO/DMPT initiator systems.
Figure 21:
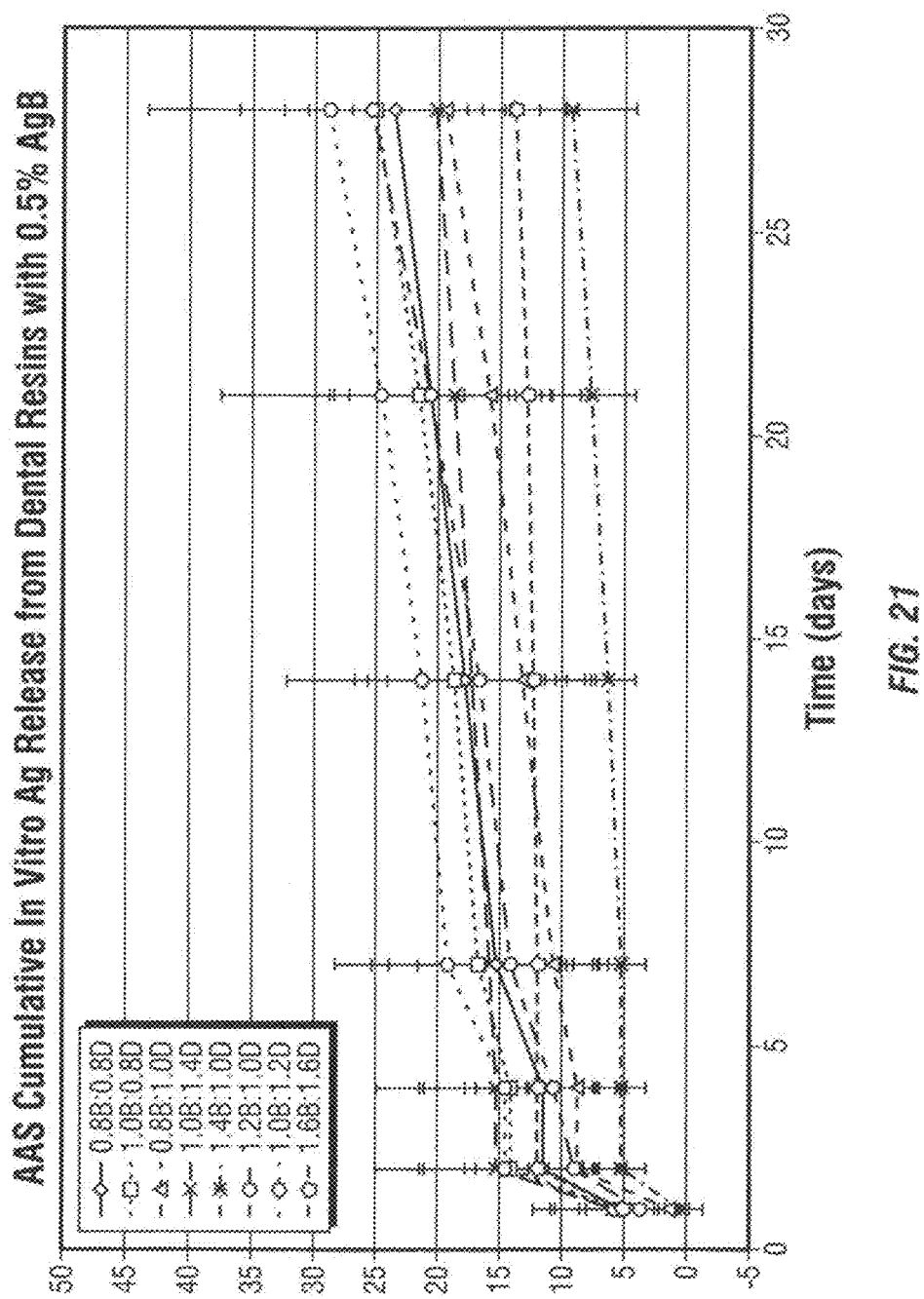
FIG. 21 illustrates in vitro Ag release studies from various anti-microbial resins with 1% AgB that were cured with BPO/DMPT initiator systems.

Results: FIGS. 20 and 21 show in vitro release of Ag measured using atomic absorption spectroscopy. 0.8B:0.8D, 1.0B:0.8D and 1.2B:1.0D formulations seem to consistently have high Ag release while the 1.6B:1.6D group, which also is the strongest mechanically, tends to release the lower amounts. Because of the high standard deviations that are often seen with release studies, only the highest releasing groups were significantly better than the least-releasing groups. Also 1% AgB samples released two to three times more Ag than 0.5% groups, possibly due to more silver nanoparticles being formed, making it easier for the Ag to diffuse out.

Conclusion: All samples released Ag. However, depending on the formulation, certain groups released more than others. However, increasing AgB concentration from 0.5 to 1% significantly increased Ag release by two to three times. 1.0B:0.8D had the highest release while the 1.6B:1.6D group, which was mechanically the strongest, was one of the slower releasing groups.

Example 6

Objective: To determine in vitro antibacterial activity of AgNP-loaded resins against bacterial species.

Methods: The subgroups chosen in Example 5 and the non-loaded resin groups (negative control) were used in a growth inhibition assay using *S. mutans* (ATCC). The bacteria was grown on TSBY (Trypticase Soy Broth with 0.5% yeast extract) agar plates in an anaerobic chamber with a mixed gas ($N_2$=85%, $H_2$=5, and $CO_2$=10%) and samples were placed on the bacteria-containing agar and anaerobically inoculated at 37° C. for 5 days to determine their efficacy in inhibiting bacterial growth by identifying any zones of inhibition.

To estimate colony formation, 20 µl of different concentrations of the bacteria (about $10^{-1}$, $10^{-2}$, $10^{-3}$, $10^{-4}$, $10^{-5}$ and $10^{-6}$/ml) were homogenously spread onto each area of the surface on the gelled TSBY agar plates by using sterile spreader. The cultures were anaerobically inoculated at 37° C. for 5 days. The colony formation was determined by countable colonies counted from suitable dilution for each sample.

Figure 22:
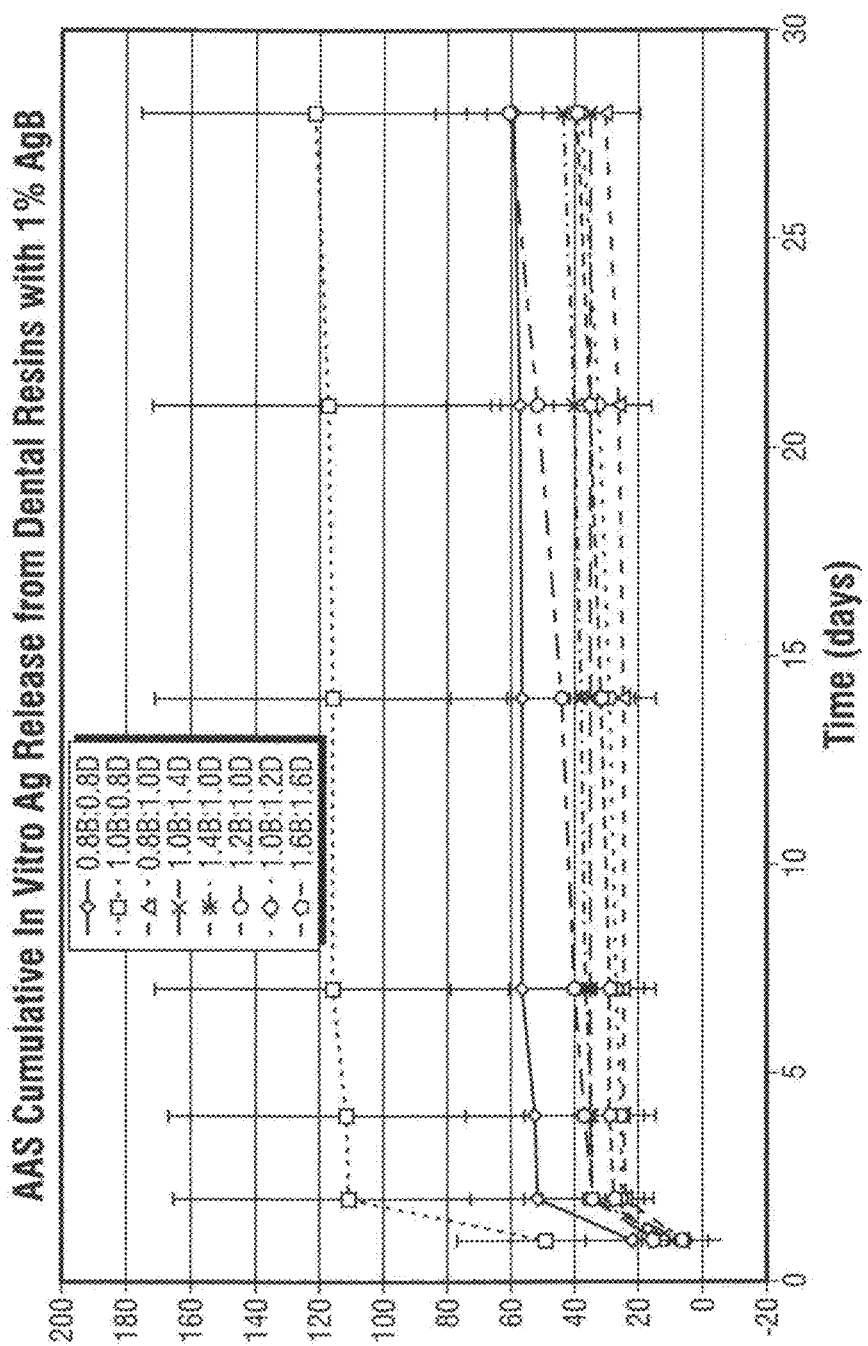
FIG. 22 shows an agar plate with BPO/DMPT-cured anti-microbial resins that contain different concentrations of AgB.
Figure 23:
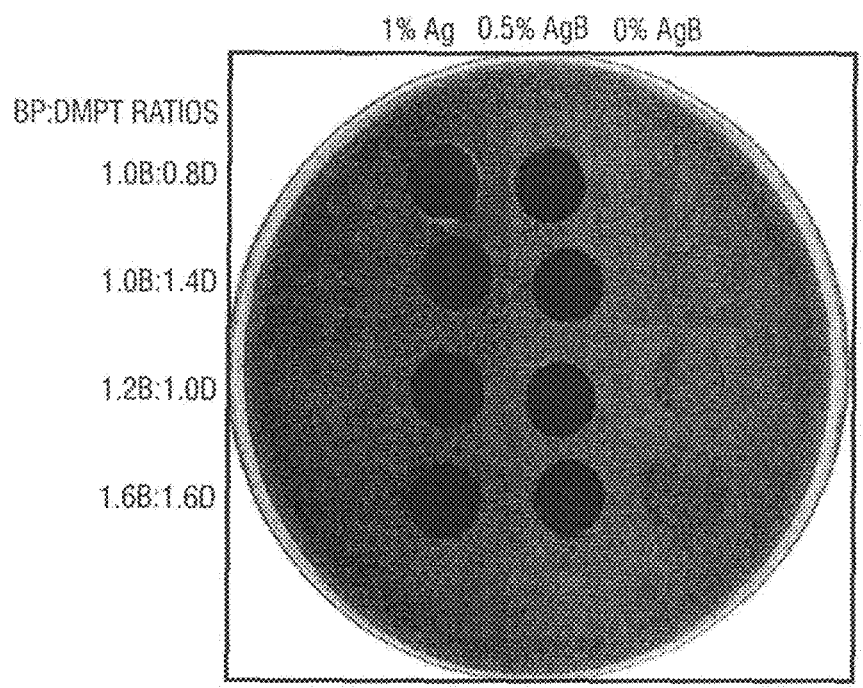
FIG. 23 shows the agar plate of FIG. 22 with the anti-microbial resins removed.

Results: FIG. 22 shows the resin specimen on the agar, and FIG. 23 shows the specimen removed and a clearer picture of the zones of inhibition. Note the dark color of the Ag-loaded specimen. It is clear that AgB concentration is directly proportional to bacterial inhibition with the 1.0B:0.8D sample giving the largest ring of inhibition, and 1.6B:1.6D inhibiting the least. By way of background, 1.0B:0.8D was the group that consistently had high Ag release in the in vitro release study in Example 3, while 1.6B:1.6D consistently had low Ag release in the same study.

Figure 24:
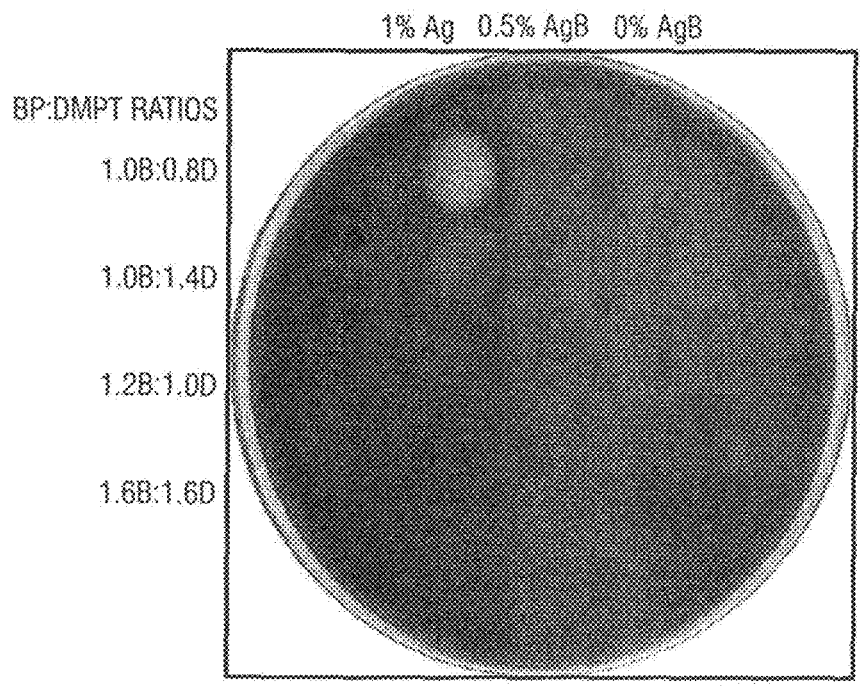
FIG. 24 illustrates the inhibitory effects of anti-microbial resins with different concentrations of Ag and BPO/DMPT initiator systems on *Streptococcus mutans*.
Figure 25:
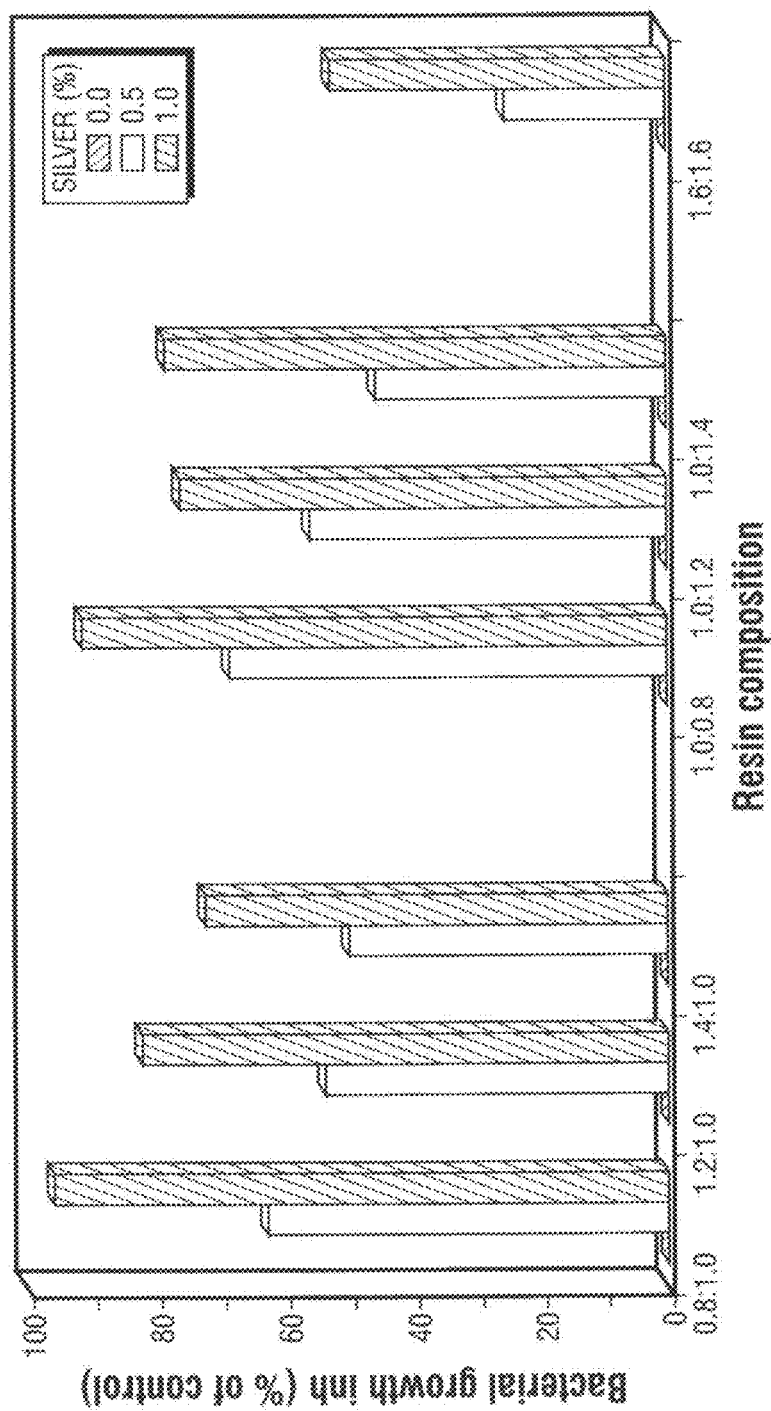
FIG. 25 graphically illustrates the correlation between resin composition and inhibition of bacterial growth shown in FIG. 24.

FIG. 24 shows the inhibitory effect of resin containing silver nanoparticles on growth of *S. mutans*. The resin composition 0.8B:1.0D and 1.0B:0.8D containing 1.0% and 0.5% AgB showed the best inhibitory activity at 95.5% and 91.6% inhibition for 1% silver and at 62.5 and 68.8% inhibition for 0.5%. Resin compositions 1.2B:1.0D and 1.0B:1.2D containing 1.0% and 0.5% of silver also gave significant inhibitory activity at 82.2% and 78.2% for 1% AgB, and 54.1% and 55.9% for 0.5% silver, respectively. The resin composition 1.6B:1.6D containing 1.0% and 0.5% AgB showed the lowest inhibitory activity at 52.5% and 25.6% inhibition, respectively. The errors are less 12% of each mean. FIG. 25 graphically illustrates the data shown in FIG. 24.

Conclusion: Both 1% and 0.5% AgB groups are able to inhibit bacterial growth, and a clear ring of inhibition can be seen with the 1.0B:0.5D sample with 1% AgB. Such a clear and large ring was not observed in the previous preliminary studies. There was some correlation to the in vitro release studies, but the mechanically strongest group (1.6B:1.6D) inhibited the bacteria least. These results also correlated well to the colony formation estimates. Thus, we have demonstrated that this technology can be used with both PMMA and Bis-GMA-based resins.

In short, a novel antimicrobial resin was made by generating AgNPs in situ using the resins own curing process. The nanoparticles of the present invention are formed during the polymerization of the resin material. As such, because antimicrobial nanoparticles are formed as the polymeric material is formed (polymerizes), better and effective incorporation is achieved.

Further analysis is needed to assess the material's biocompatibility and in vivo efficacy. Success in this work could bring about a series of antimicrobial medical and dental biomaterials that may prevent secondary caries and infection of implants.

From the foregoing detailed description of specific embodiments of the invention, it should be apparent that novel antimicrobial polymeric materials and novel methods of making such materials have been disclosed. Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. It is therefore contemplated that the claims will cover any such modifications or embodiments that fall within the true scope of the invention.

All changes to the claims that come within the meaning and range of equivalency of the claims are to be embraced within their scope. Further, all published documents, patents, and applications mentioned herein are hereby incorporated by reference, as if presented in their entirety.

What is claimed is:

1. A method of forming an antimicrobial polymeric object containing metallic nanoparticles, said method comprising:
   selecting a metal-containing material, at least one acrylic monomer and a solvent that is miscible with the metal-containing material and with the at least one acrylic monomer;
   combining the metal-containing material with the solvent to form a metal-containing material solution;
   mixing the metal containing material solution with the at least one acrylic monomer to form a mixture;
   curing the mixture to convert the monomer to a polymer, wherein the curing process forms metallic nanoparticles in situ; and
   forming an antimicrobial, polymeric object containing metallic nanoparticles.

2. The method of claim 1, wherein said metal-containing material is selected from the group consisting of silver oleates, silver gluconates, silver adipates, silver sulfadiazines, and silver acetates.

3. The method of claim 1, wherein said metal-containing material is silver benzoate.

4. The method of claim 1, wherein the monomer is selected from the group consisting of bisphenol glycidyl methacrylate (Bis-GMA), methyl methacrylate, triethylene glycol dimethacrylate (TEGDMA), 2-hydroxyethyl methacrylate (HEMA), pyromellitic acid diethylmethacrylate (PMDM), pyromellitic acid glycerol dimethacrylate (PMGDM), and urethane dimethacrylate (UDMA).

5. The method of claim 1, wherein said curing comprises a redox chemical curing process.

6. The method of claim 5, wherein said chemical curing comprises treating said mixture with benzoyl peroxide (BPO) and dimethylparatoluidine (DMPT).

7. The method of claim 5, wherein said chemical curing comprises treating said mixture with allyl thiourea (T) and cumene hydroperoxide (CH).

8. The method of claim 1, wherein said curing comprises a light curing process.

9. A method of forming an antimicrobial polymeric object containing silver nanoparticles, said method comprising:
   selecting a silver-containing material, at least one acrylic monomer and a solvent that is miscible with the metal-containing material and with the at least one acrylic monomer;
   combining the silver-containing material with the solvent to form a silver-containing material solution;
   mixing the silver-containing material solution with the at least one acrylic monomer to form a mixture;

curing the mixture to convert the acrylic monomer to a polymer, wherein the curing process forms silver nanoparticles in situ; and forming an antimicrobial, polymeric object.

10. The method of claim 9, wherein said silver-containing material is silver benzoate.

11. The method of claim 9, wherein said acrylic monomer is methyl methacrylate.

12. The method of claim 9, wherein said curing comprises a redox chemical curing process.

13. The method of claim 9, wherein said curing comprises a light curing process.

14. The method of claim 5, wherein said curing comprises a combination of light curing and chemical curing.

15. The method of claim 9, wherein said curing comprises a combination of light curing and chemical curing.

* * * * *